(12) United States Patent
Miyake et al.

(10) Patent No.: US 7,422,878 B1
(45) Date of Patent: Sep. 9, 2008

(54) **PROCESS FOR MICROBIAL PRODUCTION OF UBIQUINONE-10 USING *RHODOBACTER***

(75) Inventors: Koichiro Miyake, Hofu (JP); Shin-ichi Hashimoto, Hofu (JP); Akio Ozaki, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/110,393

(22) PCT Filed: Oct. 13, 2000

(86) PCT No.: PCT/JP00/07121

§ 371 (c)(1),
(2), (4) Date: Apr. 12, 2002

(87) PCT Pub. No.: WO01/27286

PCT Pub. Date: Apr. 19, 2001

(30) Foreign Application Priority Data

Oct. 14, 1999 (JP) ................................ 11/291959

(51) Int. Cl.
*C12P 7/66* (2006.01)
(52) U.S. Cl. ...................................... 435/133
(58) Field of Classification Search ................. 435/133, 435/193, 252.3, 252.1, 252.2
See application file for complete search history.

(56) References Cited

U.S. PATENT DOCUMENTS 6,410,280 B1 6/2002 Obata et al. ................. 435/133
2003/0219798 A1* 11/2003 Gokarn et al. ................. 435/6

FOREIGN PATENT DOCUMENTS

| JP | 06-189775 | 7/1994 |
| JP | 8-107789 | 4/1996 |
| JP | 11-56372 | 3/1999 |
| JP | 11-178590 | 7/1999 |

OTHER PUBLICATIONS

Coomber et al. (1990) Mol Microbiol 4:977-989.*
Misawa et al. (1998) J Biotechnol 59:169-181.*
Olson et al. (1983) Vitam Horm 40:4-7, 28.*
Web site for Nomenclature Committee of the International Union of Biochemistry and Molecular Biology; www.chem.qmul.ac.uk/iubmb/enzyme/search.html; accessed Aug. 3, 2004.*
Branden et al. "Introduction to Protein Structure", Garland Publishing Inc., New York, 1991, p. 247.*
Witkowski et al., Biochemistry 38:11643-11650, 1999.*
Okada, et al. "Molecular Cloning and Mutational Analysis of the DDSA Gene Encoding Decaprenyl Diphosphate Synthase . . . ", *European Journal of Biochemistry*, vol. 255, No. 1 (1998), pp. 52-59.
Lukacsovich, et al., "The Structural Basis of the High In-vivo Strength of the Ribosomal RNA . . . ", *Gene*, vol. 78, No. 1 (1989), pp. 189-194.
Zhu, et al., "Production of Ubiquinone In *Escherichia coli* by expression of Various Genes Responsible for Ubiquinone Biosynthesis", *Journal of Fermentation and Bioengineering*, vol. 79, No. 5 (1995), pp. 493-495.
Urakami, et al., "Production of ubiquinone and bacteriochlorophyll alpha by *Rhodobacter sphaeroides* and *Rhodobacter sulfidophilus*", *Journal of Fermentation and Bioengineering*, vol. 76, No. 3 (1993), pp. 191-194.
Lang, et al., "Complete DNA Sequence, Specific Tn5 Insertion Map, and Gene Assignment of Carotenoid Biosynthesis", Journal of Bacteriology, vol. 177 (1995), pp. 2064-2073.

* cited by examiner

*Primary Examiner*—David J Steadman
(74) *Attorney, Agent, or Firm*—Fitzpatrick, Cella, Harper & Scinto

(57) ABSTRACT

The present invention provides a process for producing ubiquinone-10 using a microorganism having the ability to form ubiquinone-10 and having one or more properties selected from the group consisting of the property wherein geranylgeranyltransferase activity is reduced or defective, the property wherein decaprenyldiphosphate synthetase activity is strengthened, and the property wherein p-hydroxybenzoic acid-decaprenyltransferase activity is strengthened, DNA and a polypeptide useful for the production process, microorganisms useful for the production, a method for expressing a gene in the microorganisms, and a method for breeding the microorganisms.

3 Claims, No Drawings

```
                        SEQUENCE LISTING

<160> NUMBER OF SEQ ID NOS: 12

<210> SEQ ID NO 1
<211> LENGTH: 999
<212> TYPE: DNA
<213> ORGANISM: Rhodobacter sphaeroides

<400> SEQUENCE: 1 atg gga ttg gac gag gtt tcg caa aag ccg cat gaa cgg ctc gcc gcg      48
Met Gly Leu Asp Glu Val Ser Gln Lys Pro His Glu Arg Leu Ala Ala
  1               5                  10                  15 tgg ctg gcc gag gac atg gcc gcc gtc aac ggg ctg atc cgc gag cgg      96
Trp Leu Ala Glu Asp Met Ala Ala Val Asn Gly Leu Ile Arg Glu Arg
             20                  25                  30 atg gcc tcg aaa cac gcg ccc cgc att ccc gag gtc acg gcg cat ctg     144
Met Ala Ser Lys His Ala Pro Arg Ile Pro Glu Val Thr Ala His Leu
         35                  40                  45 gtc gag gcc ggc ggc aag cgg ctg cgg ccg ctc ctg acg ctc gcc gcg     192
Val Glu Ala Gly Gly Lys Arg Leu Arg Pro Leu Leu Thr Leu Ala Ala
     50                  55                  60 gcg cgg ctc tgc ggc tac gag gga ccc tac cat atc cat ctg gcc gcg     240
Ala Arg Leu Cys Gly Tyr Glu Gly Pro Tyr His Ile His Leu Ala Ala
 65                  70                  75                  80 acg gtg gag ttc atc cac acg gcg acg ctg ctt cac gac gat gtg gtg     288
Thr Val Glu Phe Ile His Thr Ala Thr Leu Leu His Asp Asp Val Val
                 85                  90                  95 gac gag agc cac cgc cgc cgc ggc aag ccc acg gcg aac ctc ctg tgg     336
Asp Glu Ser His Arg Arg Arg Gly Lys Pro Thr Ala Asn Leu Leu Trp
            100                 105                 110 gac aac aaa tcc tcg gtg ctg gtg ggc gac tat ctc ttc gcc cgc agc     384
Asp Asn Lys Ser Ser Val Leu Val Gly Asp Tyr Leu Phe Ala Arg Ser
        115                 120                 125 ttc cag ctg atg gtc gag acc ggc tcg ctc cgc gtg atg gac atc ctc     432
Phe Gln Leu Met Val Glu Thr Gly Ser Leu Arg Val Met Asp Ile Leu
    130                 135                 140
```

```
gcc aat gcg tcg gcc acc atc tcc gag ggc gag gtg ctg caa ctg acc       480
Ala Asn Ala Ser Ala Thr Ile Ser Glu Gly Glu Val Leu Gln Leu Thr
145                 150                 155                 160 gcg gcc cag gat ctg cgc acg acc gag gac atc tac ctg cag gtg gtg       528
Ala Ala Gln Asp Leu Arg Thr Thr Glu Asp Ile Tyr Leu Gln Val Val
                165                 170                 175 cgc ggc aag acg gcc gcg ctc ttc gct gcg gcg acc cag gtg ggc ggc       576
Arg Gly Lys Thr Ala Ala Leu Phe Ala Ala Ala Thr Gln Val Gly Gly
            180                 185                 190 gtg gtc gcg ggc atg ccc gag gcg cag gtc gag gcg ctt cat gcc tac       624
Val Val Ala Gly Met Pro Glu Ala Gln Val Glu Ala Leu His Ala Tyr
        195                 200                 205 ggc gac gcg ctg ggg atc gcc ttc cag atc gtc gac gac ctc ctc gat       672
Gly Asp Ala Leu Gly Ile Ala Phe Gln Ile Val Asp Asp Leu Leu Asp
210                 215                 220 tat ggc ggc gtg gat gcc cag atc ggc aag aac acc gga gac gac ttc       720
Tyr Gly Gly Val Asp Ala Gln Ile Gly Lys Asn Thr Gly Asp Asp Phe
225                 230                 235                 240 cgc gag cgc aag ctg acg ctg ccg gtc atc aag gcg gtg gcc cag gcc       768
Arg Glu Arg Lys Leu Thr Leu Pro Val Ile Lys Ala Val Ala Gln Ala
                245                 250                 255 gat gcc gag gag cgc gcc ttc tgg cag cgg gtg atc gag aag ggc gac       816
Asp Ala Glu Glu Arg Ala Phe Trp Gln Arg Val Ile Glu Lys Gly Asp
            260                 265                 270 cag cgc gag ggg gac ctc gag cag gcc cat gcg atc atg tcc cgc cac       864
Gln Arg Glu Gly Asp Leu Glu Gln Ala His Ala Ile Met Ser Arg His
        275                 280                 285 ggc gcc atg gag gcc gcc cgg cag gat gcg ctc cgc tgg gtc gcg gtc       912
Gly Ala Met Glu Ala Ala Arg Gln Asp Ala Leu Arg Trp Val Ala Val
290                 295                 300 gcg cgc gag gca ctc ggc cag ctg ccg aag cac ccg ctg cgc gag atg       960
Ala Arg Glu Ala Leu Gly Gln Leu Pro Lys His Pro Leu Arg Glu Met
305                 310                 315                 320 ctg cac gat ctg gcc gat ttc gtg gtc gaa cgc atc gcc                   999
Leu His Asp Leu Ala Asp Phe Val Val Glu Arg Ile Ala
                325                 330
```

<210> SEQ ID NO 2
<211> LENGTH: 333
<212> TYPE: PRT
<213> ORGANISM: Rhodobacter sphaeroides

<400> SEQUENCE: 2

```
Met Gly Leu Asp Glu Val Ser Gln Lys Pro His Glu Arg Leu Ala Ala
1               5                   10                  15

Trp Leu Ala Glu Asp Met Ala Ala Val Asn Gly Leu Ile Arg Glu Arg
            20                  25                  30

Met Ala Ser Lys His Ala Pro Arg Ile Pro Glu Val Thr Ala His Leu
        35                  40                  45

Val Glu Ala Gly Gly Lys Arg Leu Arg Pro Leu Leu Thr Leu Ala Ala
    50                  55                  60

Ala Arg Leu Cys Gly Tyr Glu Gly Pro Tyr His Ile His Leu Ala Ala
65                  70                  75                  80

Thr Val Glu Phe Ile His Thr Ala Thr Leu Leu His Asp Asp Val Val
                85                  90                  95

Asp Glu Ser His Arg Arg Gly Lys Pro Thr Ala Asn Leu Leu Trp
            100                 105                 110

Asp Asn Lys Ser Ser Val Leu Val Gly Asp Tyr Leu Phe Ala Arg Ser
```

```
                  115                 120                 125
Phe Gln Leu Met Val Glu Thr Gly Ser Leu Arg Val Met Asp Ile Leu
            130                 135                 140

Ala Asn Ala Ser Ala Thr Ile Ser Glu Gly Glu Val Leu Gln Leu Thr
145                 150                 155                 160

Ala Ala Gln Asp Leu Arg Thr Thr Glu Asp Ile Tyr Leu Gln Val Val
                165                 170                 175

Arg Gly Lys Thr Ala Ala Leu Phe Ala Ala Ala Thr Gln Val Gly Gly
            180                 185                 190

Val Val Ala Gly Met Pro Glu Ala Gln Val Glu Ala Leu His Ala Tyr
                195                 200                 205

Gly Asp Ala Leu Gly Ile Ala Phe Gln Ile Val Asp Asp Leu Leu Asp
        210                 215                 220

Tyr Gly Gly Val Asp Ala Gln Ile Gly Lys Asn Thr Gly Asp Asp Phe
225                 230                 235                 240

Arg Glu Arg Lys Leu Thr Leu Pro Val Ile Lys Ala Val Ala Gln Ala
                245                 250                 255

Asp Ala Glu Glu Arg Ala Phe Trp Gln Arg Val Ile Glu Lys Gly Asp
                260                 265                 270

Gln Arg Glu Gly Asp Leu Glu Gln Ala His Ala Ile Met Ser Arg His
            275                 280                 285

Gly Ala Met Glu Ala Ala Arg Gln Asp Ala Leu Arg Trp Val Ala Val
        290                 295                 300

Ala Arg Glu Ala Leu Gly Gln Leu Pro Lys His Pro Leu Arg Glu Met
305                 310                 315                 320

Leu His Asp Leu Ala Asp Phe Val Val Glu Arg Ile Ala
                325                 330

<210> SEQ ID NO 3
<211> LENGTH: 996
<212> TYPE: DNA
<213> ORGANISM: Rhodobacter sphaeroides

<400> SEQUENCE: 3 atg cag cag ccg cgc caa gcg cca gag gct ccc gcc ggg gga ccg gcg     48
Met Gln Gln Pro Arg Gln Ala Pro Glu Ala Pro Ala Gly Gly Pro Ala
 1               5                  10                  15 gcc ggg acg acg cag ggc acg gtg gcc gat gcc ccg ccc gga aac tgg     96
Ala Gly Thr Thr Gln Gly Thr Val Ala Asp Ala Pro Pro Gly Asn Trp
                20                  25                  30 gtc gac agg ctc gcg ccc gcc gcg acg cgg ccc tat ctg cgc ctg tcg    144
Val Asp Arg Leu Ala Pro Ala Ala Thr Arg Pro Tyr Leu Arg Leu Ser
            35                  40                  45 cgc gcc gac cgg ccg atc ggg aca tgg ctt ctg ctg atc ccc tgc ttc    192
Arg Ala Asp Arg Pro Ile Gly Thr Trp Leu Leu Leu Ile Pro Cys Phe
        50                  55                  60 tgg gcg gtg gcg ctg gcg gcg ctg gcc gat ccc ggg gga tac cgg ccg    240
Trp Ala Val Ala Leu Ala Ala Leu Ala Asp Pro Gly Gly Tyr Arg Pro
 65                  70                  75                  80 ctc gac ctc tgg ctc gtg atc ggc agc tcg gtc ggc gcc ttc ctc atg    288
Leu Asp Leu Trp Leu Val Ile Gly Ser Ser Val Gly Ala Phe Leu Met
                85                  90                  95 cgc ggg gcg ggc tgc acc tgg aac gac atc acc gac cgc gag ttc gac    336
Arg Gly Ala Gly Cys Thr Trp Asn Asp Ile Thr Asp Arg Glu Phe Asp
                100                 105                 110 gcc gca gtg gca cgt acc cgc tcg cgc ccg atc ccc tcg ggg cag gtc    384
Ala Ala Val Ala Arg Thr Arg Ser Arg Pro Ile Pro Ser Gly Gln Val
```

```
                    115                 120                 125
agc gcg aag gcc gcg gcg gtc tgg atg gtg gtg cag gcg ctg gtc gcc       432
Ser Ala Lys Ala Ala Ala Val Trp Met Val Val Gln Ala Leu Val Ala
    130                 135                 140 tcg ctc atc ctc ttc agc ttc aac ggc acc gcg atc ctg ctg ggc gtg       480
Ser Leu Ile Leu Phe Ser Phe Asn Gly Thr Ala Ile Leu Leu Gly Val
145                 150                 155                 160 gcc tcg ctc gcc ctc gtc tgc atc tat ccc ttc gcc aag cgc ttc acc       528
Ala Ser Leu Ala Leu Val Cys Ile Tyr Pro Phe Ala Lys Arg Phe Thr
                165                 170                 175 tgg tgg ccg ccc ttc ctc ggg ctc gcc ttc aac tgg ggg gcg ctg ctg       576
Trp Trp Pro Pro Phe Leu Gly Leu Ala Phe Asn Trp Gly Ala Leu Leu
            180                 185                 190 ctc tgg gcc gcc cac acc ggc agc ctc ggc tgg gcg ccg gtc gcg ctc       624
Leu Trp Ala Ala His Thr Gly Ser Leu Gly Trp Ala Pro Val Ala Leu
        195                 200                 205 tat gcc tcg ggg atc gcc tgg acg ctg ttc tac gac acg atc tac gcc       672
Tyr Ala Ser Gly Ile Ala Trp Thr Leu Phe Tyr Asp Thr Ile Tyr Ala
    210                 215                 220 cat cag gac aag gag gac gat gcg ctg atc ggg gtg cgc tcg acc gcg       720
His Gln Asp Lys Glu Asp Asp Ala Leu Ile Gly Val Arg Ser Thr Ala
225                 230                 235                 240 cgg ctc ttc ggg cag cat acg ggc aag tgg ctc gtg gcc ttc atg atg       768
Arg Leu Phe Gly Gln His Thr Gly Lys Trp Leu Val Ala Phe Met Met
                245                 250                 255 gcg gcg acc ctc ctg atg acg ctc gcg gtg ctg gcc gtg ctg ccg           816
Ala Ala Thr Leu Leu Met Thr Leu Ala Val Leu Leu Ala Val Leu Pro
            260                 265                 270 cag ggc tcg atc ctc cag ctc ttg atc gca ctc gcg ggc gtc tgg ggc       864
Gln Gly Ser Ile Leu Gln Leu Leu Ile Ala Leu Ala Gly Val Trp Gly
        275                 280                 285 ttc ggc gcc cac atg acc tgg cag atc gcc cgg ctc gac acc gag gac       912
Phe Gly Ala His Met Thr Trp Gln Ile Ala Arg Leu Asp Thr Glu Asp
    290                 295                 300 acc gcg cgc tgc ctg cgc ctc ttc cgc tcg aac cgg gac gcg ggc ctg       960
Thr Ala Arg Cys Leu Arg Leu Phe Arg Ser Asn Arg Asp Ala Gly Leu
305                 310                 315                 320 atc cct gcg ctg ttt ctc gcc aca gcc gcg ctc ctt                       996
Ile Pro Ala Leu Phe Leu Ala Thr Ala Ala Leu Leu
                325                 330

<210> SEQ ID NO 4
<211> LENGTH: 332
<212> TYPE: PRT
<213> ORGANISM: Rhodobacter sphaeroides

<400> SEQUENCE: 4

Met Gln Gln Pro Arg Gln Ala Pro Glu Ala Pro Ala Gly Gly Pro Ala
1               5                   10                  15

Ala Gly Thr Thr Gln Gly Thr Val Ala Asp Ala Pro Pro Gly Asn Trp
            20                  25                  30

Val Asp Arg Leu Ala Pro Ala Ala Thr Arg Pro Tyr Leu Arg Leu Ser
        35                  40                  45

Arg Ala Asp Arg Pro Ile Gly Thr Trp Leu Leu Leu Ile Pro Cys Phe
    50                  55                  60

Trp Ala Val Ala Leu Ala Ala Leu Ala Asp Pro Gly Gly Tyr Arg Pro
65                  70                  75                  80

Leu Asp Leu Trp Leu Val Ile Gly Ser Ser Val Gly Ala Phe Leu Met
                85                  90                  95
```

```
Arg Gly Ala Gly Cys Thr Trp Asn Asp Ile Thr Asp Arg Glu Phe Asp
            100                 105                 110
Ala Ala Val Ala Arg Thr Arg Ser Arg Pro Ile Pro Ser Gly Gln Val
        115                 120                 125
Ser Ala Lys Ala Ala Val Trp Met Val Gln Ala Leu Val Ala
130                 135                 140
Ser Leu Ile Leu Phe Ser Phe Asn Gly Thr Ala Ile Leu Leu Gly Val
145                 150                 155                 160
Ala Ser Leu Ala Leu Val Cys Ile Tyr Pro Phe Ala Lys Arg Phe Thr
                165                 170                 175
Trp Trp Pro Pro Phe Leu Gly Leu Ala Phe Asn Trp Gly Ala Leu Leu
            180                 185                 190
Leu Trp Ala Ala His Thr Gly Ser Leu Gly Trp Ala Pro Val Ala Leu
        195                 200                 205
Tyr Ala Ser Gly Ile Ala Trp Thr Leu Phe Tyr Asp Thr Ile Tyr Ala
    210                 215                 220
His Gln Asp Lys Glu Asp Ala Leu Ile Gly Val Arg Ser Thr Ala
225                 230                 235                 240
Arg Leu Phe Gly Gln His Thr Gly Lys Trp Leu Val Ala Phe Met Met
                245                 250                 255
Ala Ala Thr Leu Leu Met Thr Leu Ala Val Leu Leu Ala Val Leu Pro
            260                 265                 270
Gln Gly Ser Ile Leu Gln Leu Leu Ile Ala Leu Ala Gly Val Trp Gly
        275                 280                 285
Phe Gly Ala His Met Thr Trp Gln Ile Ala Arg Leu Asp Thr Glu Asp
    290                 295                 300
Thr Ala Arg Cys Leu Arg Leu Phe Arg Ser Asn Arg Asp Ala Gly Leu
305                 310                 315                 320
Ile Pro Ala Leu Phe Leu Ala Thr Ala Ala Leu Leu
                325                 330

<210> SEQ ID NO 5
<211> LENGTH: 196
<212> TYPE: DNA
<213> ORGANISM: Rhodobacter sphaeroides

<400> SEQUENCE: 5
ggtctagact ggagccggga ttttcgagga atcgcggcct gaggtccggg cggggcaggg    60
gcgggcaggc ggtgcggcgg ctccggtgaa gtccttgcgg atcagcgggt tgcgaggaat   120
ttccatgcgg ctgtcatttt cctcttgcgg gttttttttg cggttcccta gatagcgcct   180
caccgaagga ggtacc                                                   196

<210> SEQ ID NO 6
<211> LENGTH: 1038
<212> TYPE: DNA
<213> ORGANISM: Rhodobacter sphaeroides
<220> FEATURE:
<221> NAME/KEY: CDS
<222> LOCATION: (172)..(1038)

<400> SEQUENCE: 6
aaccaccttc ggcacaatct gtctcatgcc cgggattgtt gacaccccg tgcgggctgt    60 ccagtatcaa agaccagaag gtgtaagaaa aagttgacac ctgtggagtc ggcggcacgg   120
tggccgcccc ggggcgcaac gatgcgccgg agctgtccta tgaggcacaa g atg gcg   177
                                                           Met Ala
```

```
ttt gaa cag cgg att gaa gcg gca atg gca gcg gcg atc gcg cgg ggc      225
Phe Glu Gln Arg Ile Glu Ala Ala Met Ala Ala Ala Ile Ala Arg Gly
          5                  10                  15 cag ggc tcc gag gcg ccc tcg aag ctg gcg acg gcg ctc gac tat gcg      273
Gln Gly Ser Glu Ala Pro Ser Lys Leu Ala Thr Ala Leu Asp Tyr Ala
 20                  25                  30 gtg acg ccc ggc ggc gcg cgc atc cgg ccc acg ctt ctg ctc agc gtg      321
Val Thr Pro Gly Gly Ala Arg Ile Arg Pro Thr Leu Leu Leu Ser Val
 35                  40                  45                  50 gcc acg cgc tgc ggc gac agc cgc ccg gct ctg tcg gac gcg gcg gcg      369
Ala Thr Arg Cys Gly Asp Ser Arg Pro Ala Leu Ser Asp Ala Ala Ala
                 55                  60                  65 gtg gcg ctt gag ctg atc cat tgc gcg agc ctc gtg cat gac gat ctg      417
Val Ala Leu Glu Leu Ile His Cys Ala Ser Leu Val His Asp Asp Leu
                     70                  75                  80 ccc tgc ttc gac gat gcc gag atc cgg cgc ggc aag ccc acg gtg cat      465
Pro Cys Phe Asp Asp Ala Glu Ile Arg Arg Gly Lys Pro Thr Val His
                 85                  90                  95 cgc gcc tat tcc gag ccg ctg gcg atc ctc acc ggc gac agc ctg atc      513
Arg Ala Tyr Ser Glu Pro Leu Ala Ile Leu Thr Gly Asp Ser Leu Ile
100                 105                 110 gtg atg ggc ttc gag gtg ctg gcc ggc gcg gcc gac cga ccg cag          561
Val Met Gly Phe Glu Val Leu Ala Gly Ala Ala Ala Asp Arg Pro Gln
115                 120                 125                 130 cgg gcg ctg cag ctg gtg acg gcg ctg gcg gtg cgg acg ggg atg ccg      609
Arg Ala Leu Gln Leu Val Thr Ala Leu Ala Val Arg Thr Gly Met Pro
                135                 140                 145 atg ggc atc tgc gcg ggg cag ggc tgg gag agc gag agc cag atc aat      657
Met Gly Ile Cys Ala Gly Gln Gly Trp Glu Ser Glu Ser Gln Ile Asn
                150                 155                 160 ctc tcg gcc tat cat cgg gcc aag acc ggc gcg ctc ttc atc gcc gcg      705
Leu Ser Ala Tyr His Arg Ala Lys Thr Gly Ala Leu Phe Ile Ala Ala
                165                 170                 175 acc cag atg ggc gcc att gcc gcg ggc tac gag gcc gag ccc tgg gaa      753
Thr Gln Met Gly Ala Ile Ala Ala Gly Tyr Glu Ala Glu Pro Trp Glu
180                 185                 190 gag ctg gga gcc cgc atc ggc gag gcc ttc cag gtg gcc gac gac ctg      801
Glu Leu Gly Ala Arg Ile Gly Glu Ala Phe Gln Val Ala Asp Asp Leu
195                 200                 205                 210 cgc gac gcg ctc tgc gat gcc gag acg ctg ggc aag ccc gcg ggg cag      849
Arg Asp Ala Leu Cys Asp Ala Glu Thr Leu Gly Lys Pro Ala Gly Gln
                215                 220                 225 gac gag atc cac gcc cgc ccg agc gcg gtg cgc gaa tat ggc gtc gag      897
Asp Glu Ile His Ala Arg Pro Ser Ala Val Arg Glu Tyr Gly Val Glu
                230                 235                 240 ggc gcg gcg aag ggg ctg aag gac atc ctc ggc ggc gcc atc gcc tcg      945
Gly Ala Ala Lys Gly Leu Lys Asp Ile Leu Gly Gly Ala Ile Ala Ser
                245                 250                 255 atc ccc tcc tgc ccg gcc gag gcg atg ctg gcc gag atg gtc cgc cgc      993
Ile Pro Ser Cys Pro Ala Glu Ala Met Leu Ala Glu Met Val Arg Arg
260                 265                 270 tat gcc gac aag atc gtg ccg gcg cag gtc gcg gcc cgc gtc tga         1038
Tyr Ala Asp Lys Ile Val Pro Ala Gln Val Ala Ala Arg Val
275                 280                 285

<210> SEQ ID NO 7
<211> LENGTH: 22
<212> TYPE: DNA
<213> ORGANISM: Artificial Sequence
```

```
<220> FEATURE:
<223> OTHER INFORMATION: Description of Artificial Sequence:Synthetic
      DNA

<400> SEQUENCE: 7
cgaagaagac gttgtgatgg ac                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
tctcggtcat caggcgggaa ta                                              22

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
atccayacsg cswcsctsct scayga                                          26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
tcsagsrsrt crtcsrysat gtggaa                                          26

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
ggtctagact ggagccggga ttttcgagga atc                                  33

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ggtttttttg cggttcccta gatagcgcct caccgaagga ggtaccgg                  48
```

PROCESS FOR MICROBIAL PRODUCTION OF UBIQUINONE-10 USING *RHODOBACTER*

TECHNICAL FIELD

The present invention relates to a process for producing ubiquinone-10 which is useful for improving conditions of heart disease and as a substance having an antioxidative function, DNA and a polypeptide useful for the production process, a microorganism useful for the production, expression of a novel gene in microorganisms, and a novel breeding of microorganisms.

BACKGROUND ART

Ubiquinone is a generic term for 2,3-dimethoxy-5-methyl-6-polyprenyl-1,4-benzoquinone and is also called coenzyme Q. Ubiquinone is widely present in the biological world as a component of electron transfer systems. The polyprenyl side chain of ubiquinone has a different length depending upon the biological species and homologues of ubiquinone-1 to 13 have been found in nature. The main homologues are ubiquinone-6 to 10. Many mammals including humans biosynthesize ubiquinone-10.

Ubiquinone-10 is effective for the improvement of conditions involved in cardiac failure and other ischemic cardiac disorders and has been approved as a pharmaceutical. There has been a report that this substance is effective for reducing the cardiac side effects of anti-cancer agents such as Adriamycin, and for the improvement of periodontosis, and protection of skeletal muscles against load from exercise [Bitamin no Jiten (Dictionary of Vitamins), The Vitamin Society of Japan (1996)].

In recent years, activation of energy metabolism by ubiquinone and antioxidative effect of ubiquinone nave attracted attention and its demand as a healthy food has been expanded mainly in the U.S. and Europe.

Currently, ubiquinone-10 is produced by synthetic methods or through extraction from microorganisms such as yeasts and photosynthetic bacteria. However, a more efficient production process is required due to its increased demands.

One of the effective means to form and accumulate a specific substance using a microorganism is to block the flow of an intermediate metabolite on the biosynthetic pathway leading to a targeted product toward other pathways so that more of the intermediate metabolite flows to the targeted product.

Ubiquinone is structurally divided mainly into the quinone skeleton portion and the polyprenyl side chain portion. The polyprenyl side chain is a kind of isoprenoid containing 5-carbon isopentenyl pyrophosphate (IPP) as a basic skeletal unit and is biosynthesized by condensation of a plurality of IPP.

A series of enzymes participating in this reaction is called prenyltransferases.

Prenyltransferases have been found in many biological species. For example, in *Escherichia coli*, presence of three enzymes with different length of synthetic chain, farnesyltransferase [J. Biochem., 108, (6), 995-1000 (1990)], octaprenyltransferase [J. Bac., 179, 3058-3060 (1997)], and undecaprenyltransferase [J. Bac., 181, 483-492 (1999)], has been confirmed and the gene has been identified for all of them. In *Rhodobacter* sphaeroides (hereinafter referred to as *R. sphaeroides*) which is a photosynthetic bacterium, geranylgeranyl pyrophosphate synthetase (crtE) has been identified [J. Bac., 177, 2064-2073 (1995)].

The starting substrate for prenyltransferase that supplies ubiquinone side chain is considered to be farnesyl pyrophosphate (FPP) which is also the starting substrate for the biosyntheses of various isoprenoid.

In the case of *R. sphaeroides*, it is known that a remarkable amount of carotenoid accumulates from geranylgeranyl pyrophosphate (GGPP) which is formed by the action of crtE [Biosynthesis of Isoprenoid Compounds vol. 2, JOHN WILLY & SONS (1983)].

In the genera *Pseudomonas* and *Rhodotorula*, increased ubiquinone-10 accumulation has been reported by deletion of their carotenoid producibility (Japanese Published Unexamined Patent Application Nos. 68792/82, and 39790/82).

In *R. sphaeroides*, it has been already known that the carotenoid producibility disappears where crtE is defective, but there has been no finding that such defectiveness causes a change in the amount of intracellular accumulation of ubiquinone-10 [Mol. Microbiol., 4 977-989 (1990)].

In the above literature, mutants in which carotenoid biosynthetic ability is changed are obtained by the method wherein a mutagenic treatment is given to microorganism strains using radiations such as ultraviolet rays, X-rays, and γ-rays or chemicals such as sodium nitrite, nitrosoguanidine, and ethylmethyl sulfonate; strains showing a color change are selected from the mutated strains; and strains in which the ability to biosynthesize carotenoid is defective are further selected.

To readily cause a particular enzyme activity to become defective, a method of giving a mutation directly to a gene encoding the enzyme is also used. Various methods have so far been known. Among them, a method wherein targeted enzyme activity is inactivated by disrupting the gene encoding the enzyme by incorporating a vector containing a 5'- and 3'-terminals incomplete gene into the homologous region on chromosome and a method wherein DNA containing a gene that has lost its function by entire or partial deletion, substitution or insertion of the gene is used and the gene encoding the enzyme is disrupted by transferring the deletion, substitution or insertion on the chromosome to cause the targeted enzyme activity to become defective are known for their readiness and frequent use.

For the introduction of site-directed mutation into photosynthetic bacteria including *R. sphaeroides*, a method wherein a targeted gene is disrupted by conjugational transfer using a specific *Escherichia coli* and a vector is known. However, this method involves difficulties in that only limited vectors can be used and the separation process between *Escherichia coli* and a photosynthetic bacterium after conjugation is complicated. Construction of a site-directed homologous recombinant technique that is widely applicable regardless the kind of vectors is desired.

Another effective means to form and accumulate a specific substance using microorganisms is to strengthen the expression of an enzyme gene on the biosynthetic pathway.

In the case of ubiquinones, p-hydroxybenzoic acid biosynthesized via chorismic acid that is biosynthesized through the shikimic acid pathway is the starting substrate for the quinone skeleton portion. On the other hand, the starting substrate for the polyprenyl side chain portion is polyprenyl diphosphate formed by condensation of a plurality of IPP biosynthesized through the mevalonic acid pathway or through the recently clarified non-mevalonic acid pathway [Biochem. J., 295, 517 (1993)]. p-Hydroxybenzoic acid and polyprenyl diphosphate are converted to 4-hydroxy-3-polyprenylbenzoic acid by the action of p-hydroxybenzoic acid-polyprenyltransferase (EC.2.5.1.39), which undergoes various modifications to be converted to ubiquinone.

These enzymes on the biosynthetic pathways and their genes have been mostly identified in *Escherichia coli* and yeasts. Although the whole aspect of these genes have not yet been elucidated, several examples showing an increased accumulation of ubiquinone by strengthening the expression of enzyme genes on the biosynthetic pathway of ubiquinone are known. For example, Zhu et al. showed that the amount of ubiquinone accumulation increased by linking various enzyme genes of ubiquinone biosynthesis derived from *Escherichia coli* downstream to lac promoter and highly expressing them in *Escherichia coli* [J. Fermentation and Bioengineering, 79, 493 (1995)]. Also, Kawamukai et al. showed an improved productivity of ubiquinone-10 by introducing ubiA and ubiC derived from *Escherichia coli* into a photosynthetic bacterium, *R. capsulatus*, and carrying out culturing unaerobically (Japanese Published Unexamined Patent Application No. 107789/96)].

However, where the rate limiting step is in the biosynthesis of ubiquinone and what control does it undergo are yet to be elucidated.

To strengthen the biosynthetic system of ubiquinone in photosynthetic bacteria, it is considered to be most suitable to use enzyme genes of photosynthetic bacteria themselves. However, almost no enzyme gene that participates in the biosynthesis of ubiquinone is known with photosynthetic bacteria.

In order to strengthen the biosynthetic system of ubiquinone in photosynthetic bacteria, it is important to specify the rate limiting step on the biosynthetic pathway, isolate genes on the biosynthetic pathway of ubiquinone including the gene involved in the rate limiting step, and determine the nucleotide sequence of and around the genes.

DISCLOSURE OF THE INVENTION

An object of the present invention is to provide an industrially useful process for producing ubiquinone-10 which is useful for improving conditions of heart disease and as a substance having an antioxidative function, DNA and polypeptides useful for the production process, microorganisms useful for the production, expression of genes in the microorganisms, and a process for breeding the microorganisms.

The present inventors made an intensive investigation into industrially useful processes for the production of ubiquinone-10. As a result, they have found genes involved in the improvement of ubiquinone-10 biosynthesis in microorganisms belonging to photosynthetic bacteria.

The present invention has been completed on the basis of this result.

The present invention relates to the following (1)-(41).

(1) A process for producing ubiquinone-10 which comprises culturing, in a medium, a microorganism having the ability to form ubiquinone-10 and having one or more properties selected from the group consisting of the property wherein geranylgeranyl pyrophosphate synthetase activity is reduced or defective, the property wherein decaprenyldiphos-phate synthetase activity is strengthened, and the property wherein p-hydroxybenzoic-acid-decaprenyl-transterase activity is strengthened, allowing ubiquinone-10 to form and accumulate in a culture, and recovering the ubiquinone-10 from the culture.

(2) The process according to the above (1), wherein the property wherein geranylgeranyl pyrophosphate synthetase activity is reduced or defective is a property obtained by introducing DNA comprising a nucleotide sequence wherein one or more nucleotide residues have been deleted, substituted or added in the nucleotide sequence of DNA encoding geranylgeranyl pyrophosphate synthetase, and encoding a polypeptide wherein geranylgeranyl pyrophosphate synthetase activity is reduced or defective into a microorganism having the ability to form ubiquinone-10.

Deletion, substitution or addition of a nucleotide residue referred to in the present specification can be carried out by site-directed mutagenesis which is a technique known prior to the present application. More particularly, they can be performed in accordance with methods described in Molecular Cloning, A Laboratory Manual, Second Edition (Edited by: Sambrook, Fritsch and Maniatis), Cold Spring Harbor Laboratory Press (1989) (hereinafter referred to as Molecular Cloning, Second Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985); etc.

(3) The process according to the above (2), wherein the DNA encoding geranylgeranyl pyrophosphate synthetase is DNA encoding geranylgeranyltransferase derived from *Rhodobacter sphaeroides*.

(4) The process according to the above (2), wherein the DNA encoding geranylgeranyl pyrophosphate synthetase is DNA comprising the nucleotide sequence shown in SEQ ID NO: 6.

(5) The process according to the above (1), wherein the property wherein decaprenyldiphosphate synthetase activity is strengthened is a property which is obtained by introducing DNA encoding decaprenyldiphosphate synthetase into a microorganism having the ability to form ubiquinone-10.

(6) The process according to the above (5), wherein the DNA encoding decaprenyldiphosphate synthetase is DNA encoding decaprenyldiphosphate synthetase derived from *Rhodobacter sphaeroides*.

(7) The process according to the above (5), wherein the DNA encoding decaprenyldiphosphate synthetase is DNA encoding a polypeptide selected from the following (a), (b) and (c):
  (a) a polypeptide comprising the amino acid sequence shown in SEQ ID NO: 2,
  (b) a polypeptide comprising an amino acid sequence wherein one or more amino acid residues have been deleted, substituted or added in the amino acid sequence of the polypeptide of the above (a) and having decaprenyldiphosphate synthetase activity, and
  (c) a polypeptide comprising an amino acid sequence having at least 60% homology to the amino acid sequence shown in SEQ ID NO: 2 and having decaprenyldiphosphate synthetase activity.

As in the case of deletion, substitution or addition of nucleotide residues described above, deletion, substitution or addition of amino acid residues referred to herein can be carried out by site-directed mutagenesis which is a technique known prior to the present application. The number of amino acid residues which are deleted, substituted or added is not specifically limited, but is preferably within the range of one to several decades, more preferably one to several.

In order for the above decaprenyldiphosphate synthetase to maintain the enzyme activity, it is preferable that the homology possessed by the amino acid sequence of the polypeptide is at least 60%, generally 80%, and preferably 95% or more.

Homology referred to herein can be calculated using a homology analyzing program such as BLAST [J. Mol. Biol., 215, 403 (1990)], FASTA [Methods Enzymol., 183, 63 (1990)], etc.

(8) The process according to the above (5), wherein the DNA encoding decaprenyldiphosphate synthetase is DNA of the following (a) or (b):
  (a) DNA comprising the nucleotide sequence shown in SEQ ID NO: 1, or
  (b) DNA which hybridizes to the DNA of the above (a) under stringent conditions and which encodes a polypeptide having decaprenyldiphosphate synthetase activity.

The description "DNA which hybridizes under stringent conditions" as used herein refers to DNA which is obtained by colony hybridization, plaque hybridization or Southern blot hybridization using the DNA of the present invention or a fragment thereof as a probe. Such DNA can be identified, for example, by performing hybridization at 65° C. in the presence of 0.7-1.0 mol/l NaCl using a filter with colony- or plaque-derived DNA or a fragment thereof immobilized thereon and then washing the filter at 65° C. using 0.1 to 2-fold concentrated SSC solution (1-fold concentrated SSC solution; 150 mmol/l sodium chloride and 15 mmol/l sodium citrate).

Hybridization can be carried out according to the method described in Molecular Cloning, Second Edition. The hybridizable DNA of the above DNA is, for example, DNA having at least 70% homology, preferably 90% or more homology to the nucleotide sequence shown in SEQ ID NO: 1.

(9) The process according to the above (1), wherein the property wherein p-hydroxybenzoic acid-decaprenyltransferase activity is strengthened is a property which is obtained by introducing DNA encoding p-hydroxybenzoic acid-decaprenyltransferase into a microorganism having the ability to form ubiquinone-10.

(10) The process according to the above (9), wherein the DNA encoding p-hydroxybenzoic acid-decaprenyltransferase is DNA encoding p-hydroxybenzoic acid-decaprenyltransferase derived from *Rhodobacter sphaeroides*.

(11) The process according to the above (9), wherein the DNA encoding p-hydroxybenzoic acid-decaprenyltransferase is DNA encoding a polypeptide selected from the following (a), (b) and (c):
  (a) a polypeptide comprising the amino acid sequence shown in SEQ ID NO: 4,
  (b) a polypeptide comprising an amino acid sequence wherein one or more amino acid residues have been deleted, substituted or added in the amino acid sequence of the polypeptide of the above (a) and having p-hydroxybenzoic acid-decaprenyltransferase activity, and
  (c) a polypeptide comprising an amino acid sequence having at least 60% homology to the amino acid sequence shown in SEQ ID NO: 4 and having p-hydroxybenzoic acid-decaprenyltransferase activity.

In order for the above polypeptide having p-hydroxybenzoic acid-decaprenyltransferase activity to maintain the activity of the polypeptide, it is preferred that the homology possessed by the amino acid sequence of the polypeptide is at least 60%, generally 80%, and particularly 95% or more.

(12) The process according to the above (9), wherein the DNA encoding p-hydroxybenzoic acid-decaprenyltransferase is DNA of the following (a) or (b):
  (a) DNA comprising the nucleotide sequence shown in SEQ ID NO: 3, or
  (b) DNA which hybridizes to the DNA of the above (a) under stringent conditions and which encodes a polypeptide having p-hydroxybenzoic acid-decaprenyltransferase activity.

The hybridizable DNA of the above DNA is, for example, DNA having at least 70% homology, preferably 90% or more homology to the nucleotide sequence shown in SEQ ID NO: 3.

(13) The process according to any of the above (1), (2), (5) or (9), wherein the microorganism having the ability to form ubiquinone-10 is selected from the group consisting of microorganisms belonging to the genus *Agrobacterium*, microorganisms belonging to the genus *Paracoccus*, and microorganisms belonging to photosynthetic bacteria.

(14) The process according to the above (13), wherein the microorganisms belonging to photosynthetic bacteria are microorganisms selected from the group consisting of microorganisms belonging to the genus *Rhodobacter*, the genus *Rhodomicrobium*, the genus *Rhodopila*, the genus *Rhodospirillum*, or the genus *Rhodopseudomonas*.

(15) The process according to the above (14), wherein the microorganisms belonging to the genus *Rhodobacter* are microorganisms belonging to the species *Rhodobacter sphaeroides* or *Rhodobacter capsulatus*.

(16) The process according to any of the above (2), (5) and (9), wherein introduction of the DNA into a host microorganism belonging to the genus *Rhodobacter* carried out by electroporation.

(17) Decaprenyldiphosphate synthetase which is derived from *Rhodobacter sphaeroides*.

(18) A polypeptide selected from the following (a), (b), and (c):
  (a) a polypeptide comprising the amino acid sequence shown in SEQ ID NO; 2,
  (b) a polypeptide comprising an amino acid sequence wherein one or more amino acid residues have been deleted, substituted or added in the amino acid sequence of the polypeptide of the above (a) and having decaprenyldiphosphate synthetase activity, and
  (c) a polypeptide comprising an amino acid sequence having at least 60% homology to the amino acid sequence shown in SEQ ID NO: 2 and having decaprenyldiphosphate synthetase activity.

(19) p-Hydroxybenzoic acid-decaprenyltransferase which is derived from *Rhodobacter sphaeroides*.

(20) A polypeptide selected from the following (a), (b) and (c):
  (a) a polypeptide comprising the amino acid sequence shown in SEQ ID NO: 4,
  (b) a polypeptide comprising an amino acid sequence wherein one or more amino acid residues have been deleted, substituted or added in the amino acid sequence of the polypeptide of the above (a) and having p-hydroxybenzoic acid-decaprenyltransferase activity, and
  (c) a polypeptide comprising an amino acid sequence having at least 60% homology to the amino acid sequence shown in SEQ ID NO: 4 and having p-hydroxybenzoic acid-decaprenyltransferase activity.

(21) DNA selected from the following (a), (b) and (c):
  (a) DNA which encodes the polypeptide of the above (17) or (18),
  (b) DNA comprising the nucleotide sequence shown in SEQ ID NO: 1, and
  (c) DNA which hybridizes to the DNA of the above (a) or (b) under stringent conditions and which encodes a polypeptide having decaprenyldiphosphate synthetase activity.

(22) DNA selected from the following (a), (b) and (c):
  (a) DNA which encodes the polypeptide of the above (19) or (20), (b) DNA comprising the nucleotide sequence shown in SEQ ID NO: 3, and
(c) DNA which hybridizes to the DNA of the above (a) or (b) under stringent conditions and which encodes a polypeptide having p-hydroxybenzoic acid-decaprenyl-transferase activity.
(23) Recombinant DNA which is obtained by inserting the DNA of the above (21) or (22) into a vector.
(24) The recombinant DNA according to the above (23), wherein the DNA is inserted downstream to DNA comprising a nucleotide sequence of a promoter which is present in a ribosomal RNA gene.
(25) The recombinant DNA according to the above (24), wherein the ribosomal RNA gene is a ribosomal RNA gene which is derived from a microorganism belonging to the genus *Rhodobacter*.
(26) The recombinant DNA according to the above (24), wherein the DNA which comprises a nucleotide sequence of a promoter is DNA comprising the nucleotide sequence shown in SEQ ID NO: 5.
(27) A transformant which carries the recombinant DNA according to any one of the above (23) to (26).
(28) The transformant according to the above (27), wherein the transformant is a microorganism having the ability to form ubiquinone-10.
(29) The transformant according to the above (28), wherein the microorganism having the ability to form ubiquinone-10 is a microorganism selected from the group consisting of microorganisms belonging to the genus *Agrobacterium*, microorganisms belonging to the genus *Paracoccus*, and microorganisms belonging to photosynthetic bacteria.
(30) The transformant according to the above (29), wherein the microorganisms belonging to photosynthetic bacteria are microorganisms selected from the group consisting of microorganisms belonging to the genus *Rhodobacter*, the genus *Rhodomicrobium*, the genus *Rhodopila*, the genus *Rhodospirillum*, and the genus *Rhodopseudomonas*.
(31) The transformant according to the above (30), wherein the microorganisms belonging to the genus *Rhodobacter* are microorganisms belonging to the species *Rhodobacter sphaeroides* or *Rhodobacter capsulatus*.
(32) A process for producing ubiquinone-10, which comprising culturing the transformant according to any one of the above (27) to (31) in a medium, allowing ubiquinone-10 to form and accumulate in the culture, and recovering the ubiquinone-10 from the culture.
(33) A process for expressing DNA encoding a polypeptide of interest, which comprises inserting DNA encoding the polypeptide downstream to DNA which comprises a nucleotide sequence of a promoter which is present in a ribosomal RNA gene.
(34) The process for expressing a gene according to the above (33), wherein the ribosomal RNA gene is a ribosomal RNA gene which is derived from a microorganism belonging to the genus *Rhodobacter*.
(35) The process for expressing a gene according to the above (34), wherein the DNA which comprises a nucleotide sequence of a promoter is DNA having the nucleotide sequence shown in SEQ ID NO: 5.
(36) The process for expressing a gene according to any one of the above (33) to (35), wherein the expression is effected in a microorganism having the ability to form ubiquinone-10.
(37) A process for constructing a mutant of a microorganism having the ability to form ubiquinone-10, which comprises introducing DNA having a nucleotide sequence wherein one or more nucleotide residues have been deleted, substituted or added in the nucleotide sequence of DNA encoding a polypeptide derived from a microorganism having the ability to form ubiquinone-10 and encoding a polypeptide of which the polypeptide activity has been altered, into a microorganism having the ability to form ubiquinone-10 by electroporation.
(38) The process according to the above (37), wherein the DNA encoding a polypeptide derived from a microorganism having the ability to form ubiquinone-10 is DNA comprising the nucleotide sequence shown in SEQ ID NO: 6.
(39) The process according to any one of the above (36) to (38), wherein the microorganism having the ability to form ubiquinone-10 is a microorganism selected from the group consisting of microorganisms belonging to the genus *Agrobacterium*, microorganisms belonging to the genus *Paracoccus*, and microorganisms belonging to photosynthetic bacteria.
(40) The process according to the above (39), wherein the microorganisms belonging to photosynthetic bacteria are microorganisms selected from the group consisting of microorganisms belonging to the genus *Rhodobacter*, the genus *Rhodomicrobium*, the genus *Rhodopila*, the genus *Rhodospirillum*, or the genus *Rhodopseudomonas*.
(41) The process according to the above (40), wherein the microorganisms belonging to the genus *Rhodobacter* are microorganisms belonging to the species *Rhodobacter sphaeroides* or *Rhodobacter capsulatus*.

The present invention is described in detail below.

[1] Construction of a Microorganism in which Geranylgeranyl Pyrophosphate Synthetase (crtE) Activity is Reduced or Defective For the construction of a microorganism in which crtE activity is reduced or defective according to the present invention, any microorganisms having the ability to form ubiquinone-10 can be used. For example, microorganisms belonging to the genus *Agrobacterium* or *Paracoccus*, and those belonging to photosynthetic bacteria may be used.

Examples of suitable microorganisms belonging to photosynthetic bacteria are those belonging to the genus *Rhodobacter*, *Rhodomicrobium*, *Rhodopila*, *Rhodospirillum*, or *Rhodopseudomonas*, specifically, *Rhodobacter sphaeroides* and *Rhodobacter capsulatus*, and more specifically, *R. sphaeroides* ATCC17023 and *R. sphaeroides* FERM BP-4675.

Construction of a microorganism having the ability to form ubiquinone-10 in which crtE activity is reduced or defective is carried out by a method wherein a microorganism having the ability to form ubiquinone-10 is subjected to a mutagenic treatment according to a conventional method using radiation such as ultraviolet rays, X-rays and γ-rays or chemicals such as sodium nitrite, nitrosoguanidine, and ethylmethyl sulfonate and strains in which crtE activity is reduced or defective are selected from the strains whose colonies show color change when grown on an agar medium.

For example, while wild-type strains form red colonies due to accumulation of carotenoid, the color tone of colonies formed by the above mutants is variable showing pink, yellow or light violet depending on the site the gene is deleted, therefore, the targeted mutants can be selected based on the color tone of the colonies.

The targeted strains can also be obtained using a method of introducing mutation directly into a gene encoding crtE using genetic engineering techniques.

The method for obtaining the targeted strains by introducing mutation directly into the gene encoding crtE using genetic engineering techniques is explained in detail below.

(1) Extraction of Chromosomal DNA from a Microorganism Having the Ability to Form Ubiquinone-10

Chromosomal DNA can be extracted from a microorganism having the ability to form ubiquinone-10, for example, according to the method described in Molecular and General Genetics, 213, 78-83 (1988) or in Nucleic Acids Res., 18, 7267 (1990).

(2) Isolation of a DNA Fragment Containing the crtE Gene Derived from a Microorganism Having the Ability to Form Ubiquinone-10

The nucleotide sequence of an enzyme gene cluster participating in carotenoid biosynthesis containing crtE of *R. sphaeroides* has already been published [J. Bacteriology, 177, 2064-2073 (1995)]. Primer DNA is prepared based on the nucleotide sequence information by, for example, using a DNA synthesizer.

Using the primer DNA, any DNA fragment containing crtE can be isolated according to PCR using chromosomal DNA derived from the microorganism having the ability to form ubiquinone-10 obtained in (1) above as a template.

An example of the sense primer to be used for PCR is the sequence shown in SEQ ID NO: 7 and that of the antisense primer is the sequence shown in SEQ ID NO: 8. By the combination of these primers, in addition to ORF encoding crtE, full length of the crtE gene containing upstream and downstream regions of crtE can be amplified.

As the DNA polymerase to be used for PCR, commercially available enzymes, for example, Takara Taq DNA polymerase (Takara Shuzo Co., Ltd.), TAKARA LA-PCR™ Kit Ver. 2 (Takara Shuzo Co., Ltd.) and EXPAND™ High-Fidelity PCR System (Boehringer Mannheim) can be used, while Takara PCR thermal cycler 480 (Takara Shuzo Co., Ltd.) can be used for carrying out PCR.

PCR is carried out, for example, by 30 cycles, one cycle consisting of reaction at 94° C. for 30 seconds, reaction at 55° C. for 30 seconds to one minute and reaction at 72° C. for 2 minutes where DNA fragments of 2 kb or less are amplified, and of reaction at 98° C. for 20 seconds and reaction at 68° C. for 3 minute where DNA fragments over 2 kb are amplified, respectively, followed by reaction at 72° C. for 7 minutes.

The resulting amplified DNA fragment is separated and isolated by agarose gel electrophoresis or other techniques.

The amplified DNA fragment separated and isolated is extracted and purified from agarose gel using, for example, Mermaid kit (Bio 101 Inc. CA., USA).

The purified DNA is linked to a suitable vector, for example, pCR2.1 (Invitrogen) using, for example, TA cloning kit (Invitrogen).

The DNA can also be linked to a suitable vector that is replicable in *Escherichia coli* according to the following method.

The amplified DNA fragment obtained above, and a suitable vector replicable in *Escherichia coli* are cleaved with restriction enzymes that recognize the restriction enzyme sites provided by the above primers. The resulting cleaved DNA fragments are fractionated and recovered by agarose gel electrophoresis, respectively. The DNA fragments with both ends cleaved are linked according to a conventional method.

An appropriate host, *Escherichia coli*, for example, INVαF' (Invitrogen) and DH5α (Toyobo Co., Ltd.), is transformed with the plasmid obtained by linking to the vector according to the above method.

Transformants can be selected by spreading the cells on agar medium containing a drug to which a drug resistance gene carried by the vector is resistant, for example, LB agar medium containing 100 μg/ml ampicillin, and culturing overnight at 37° C.

Plasmid containing targeted DNA is obtained from the transformant strains thus obtained, for example, by the method described in Molecular Cloning, Second Edition.

The nucleotide sequence of the PCR-amplified fragment region contained in the obtained plasmid can be determined using, for example, DyeTerminator Cycle Sequencing FS Ready Reaction Kit (Perkin-Elmer Japan) and 373A Sequencer (Perkin-Elmer Japan).

It is possible to confirm that the amplified sequence contains ctrE by comparing the nucleotide sequence of the amplified sequence with information on the known sequence.

(3) Preparation of a Microorganism Having the Ability to Form Ubiquinone-10 in which crtE Activity is Reduced or Defective Microorganisms having the ability to form ubiquinone-10 in which crtE activity is reduced or defective can be obtained based on the DNA encoding crtE obtained according to (2) above or information on its nucleotide sequence.

Reduction or defectiveness of crtE activity in photosynthetic bacteria can be achieved by causing the crtE gene present on chromosomal DNA to undergo entire or partial deletion, substitution or addition mutation. It can also be caused by suppressing the expression of the crtE gene.

In causing entire or partial deletion, substitution or addition mutation in the crtE gene present on chromosome, any methods usually used for introducing mutation can be used.

For example, the following methods (a) and (b) can be used.

(a) A method wherein circular DNA containing DNA in which 5'- and 3'-terminals of the crtE gene are deleted is introduced into the targeted strain and recombination is allowed to be effected between the introduced DNA and a homologous region on the corresponding chromosomal DNA, thereby causing the gene on the chromosome to be incomplete.

In this method, deletion of 5'- and 3'-terminals may be any kind so long as crtE activity of the strain that have undergone recombination decreases or become defective. Instead of deletion of a 5'-terminal, it is also possible to use deletion of the region that is necessary for the transcription of the gene or of the region that is necessary for the translation of the crtE protein.

Preferred circular DNA is one that contains a marker gene, such as a drug resistance gene to facilitate selection of recombinant strains, and, at the same time, is incapable of self amplification in the strain into which it is introduced to suppress the expression of the marker gene in strains other than recombinant strains or becomes non-replicable under certain conditions as in the case of plasmid having a temperature sensitive replication region. The circular DNA may have replicability in strains other than the strain into which it is to be introduced.

1. A method wherein DNA containing a mutated gene in which entire or partial deletion, substitution or addition mutation has been caused to the crtE gene is introduced into the targeted strain and recombination is allowed to be effected between the region encompassing the two sites of the deletion, substitution or addition mutation and the corresponding homologous region on chromosome, thereby introducing the deletion, substitution or addition into a gene on chromosome.

In this method, the deletion, substitution or addition mutation carried by the mutated gene to be introduced may be any kind so long as the mutation causes crtE activity of the strain in which such mutation is introduced into the gene on its chromosome to be reduced or become defective.

DNA in which the deletion, substitution or addition is introduced into the region necessary for the replication of the gene or the region necessary for the translation of the crtE protein can also be used so long as the mutation causes crtE activity of the strain in which such mutation is introduced into the gene on its chromosome to be reduced or become defective.

It is preferred, also in this method, to use circular DNA containing the above DNA and having the properties described in the above (a) to facilitate selection of recombinant strains.

Introduction of a DNA fragment into photosynthetic bacteria can be performed by a method of conjugational transfer, for example, according to the methods described in Bio/Technology, 1, 784-791 (1983), and Gene, 118, 145-146 (1992). It is also possible to use electroporation that can be carried out using commercially available apparatus, for example, Gene Pulser II (Biorad).

The strains in which crtE activity is reduced or defective can be selected using, as a marker, a drug resistance expressed by a drug resistance gene that is simultaneously incorporated into chromosome. Furthermore, the targeted strains can be obtained by selecting the strains whose colonies show color change due to reduction or defectiveness of the ability to synthesize carotenoid.

It is possible to confirm that the mutation is introduced into the crtE gene by introducing the normal crtE gene isolated in (2) above into the above strains in which crtE activity is reduced or deleted and checking whether or not the ability to biosynthesize carotenoid is recovered.

[2] Cloning of the Decaprenyldiphosphate Synthetase Gene Derived from a Microorganism Having the Ability to Form Ubiquinone-10

DNA encoding decaprenyldiphosphate synthetase of the present invention can be obtained from the microorganisms having the ability to form ubiquinone-10 described in [1] above according to the following method.

(1) Isolation of a Partial Fragment of the Decaprenyldiphosphate Synthetase Gene DNA containing a partial fragment of the decaprenyldiphosphate synthetase gene derived from the microorganism having the ability to form ubiquinone-10 can be obtained by selecting two or more regions having a high homology in known amino acid sequences of the polyprenyldiphosphate synthetase gene and carrying out PCR using an oligodeoxynucleotide containing a nucleotide sequence encoding the selected amino acid sequence as a sense primer, an oligodeoxynucleotide containing a sequence complementary to a nucleotide sequence encoding the selected amino acid sequence as an antisense primer, and chromosomal DNA of the microorganism as a template.

Examples of known sequences of the polyprenyldiphosphate synthetase gene are those derived from *Bacillus subtilis, Bacillus stearothermophilus, Escherichia coli, Gluconobacter suboxydans, Haemophilus influenzae, Hericobacter pylori, Rhodobacter capsulatus, Saccharomyces serevisiae, Schizosaccharomyces pombe* and *Synechocystis* sp. PCC6803. These sequences are available from the data bases of public organizations, for example, GenBank.

An example of the sense primer to be used for PCR is the sequence shown in SEQ ID NO: 9 and an example of the anti-sense primer is the sequence shown in SEQ ID NO: 10.

These oligodeoxynucleotides can be synthesized using a DNA synthesizer generally used.

As the DNA polymerase to be used for PCR, commercially available enzymes, for example, Takara Taq DNA polymerase (Takara Shuzo Co., Ltd.) can be used, while Takara PCR thermal cycler 480 (Takara Shuzo Co., Ltd.), etc. can be used for carrying out PCR.

PCR is carried out, for example, by 5 cycles, one cycle consisting of reaction at 94° C. for 45 seconds, reaction at 35° C. for 45 seconds, and reaction at 72° C. for one minute, followed by 30 cycles, one cycle consisting of reaction at 94° C. for 45 seconds, reaction at 45° C. for 45 seconds, and reaction at 72° C. for one minute.

Isolation, and purification of amplified DNA fragments, linking thereof to a suitable vector, transformation with a recombinant DNA obtained by such linking and preparation of transformants, preparation of plasmid DNA containing targeted DNA from the obtained transformant strains, and determination of the nucleotide sequence of a PCR amplified fragment region contained in the obtained plasmid DNA can be carried out in accordance with the methods described in [1] above.

It is possible to confirm that the amplified sequence contains the polyprenyldiphosphate synthetase gene by comparing the nucleotide sequence of the amplified sequence with information on known sequences.

(2) Isolation of the Full Length Gene Using a Partial Fragment of the Polyprenyldiphosphate Synthetase Gene A DNA fragment containing the entire decaprenyldiphosphate synthetase gene derived from the microorganism having the ability to form ubiquinone-10 can be isolated from a genome library derived from the microorganism having the ability to form ubiquinone-10 using DNA having a partial sequence of the gene according to, for example, the following method.

Chromosomal DNA derived from the microorganism having the ability to form ubiquinone-10 is subjected to extraction in accordance with the method described in [1](1) above and then to partial digestion with a suitable restriction enzyme such as Sau 3AI. The resulting digested DNA fragment is fractionated using a conventional method such as sucrose density gradient ultracentrifugation.

30 to 40 kb DNA fragments obtained by the fractionation are linked to a cosmid vector, for example, SuperCosI, which has been digested with a suitable restriction enzyme such as Bam HI, for packaging in λ phage.

Using the thus prepared recombinant phage, a chromosomal DNA library is prepared by transformation of a suitable host cell, for example, *Escherichia coli* DH5α according to a conventional method (for example, the method described in Molecular Cloning, Second Edition) and obtaining transformants.

The transformants can be selected by spreading the cells on an agar medium containing a drug to which a drug resistance gene carried by the vector is resistant, for example, LB agar medium containing 100 μg/ml ampicillin, and culturing overnight at 37° C.

Of cosmids which the transformants contain, the cosmid having a DNA fragment containing the entire decaprenyldiphosphate synthetase gene derived from the microorganism having the ability to form ubiquinone-10 can be confirmed by Southern hybridization using the following DNA as a probe.

DNA to be used as the probe can be prepared using DNAs containing the entire or a part of the nucleotide sequence determined in [2] (1) above and DIG oligonucleotide Tailing Kit (Boehringer Mannheim). The targeted DNA can be detected using the probe and DIG DNA Detection Kit (Boehringer Mannheim).

It is also possible to confirm the cosmid which contains a DNA fragment containing the entire decaprenyldiphosphate synthetase gene by the presence of the amplified fragment on the basis of PCR using the cosmid extracted from the transformant obtained above as a template, and a sense primer and an anti-sense primer designed based on a partial sequence of the decaprenyldiphosphate synthetase gene previously determined.

A DNA fragment containing the decaprenyldiphosphate synthetase gene can be isolated and recovered by agarose gel electrophoresis after digestion of the cosmid containing the DNA fragment with a restriction enzyme.

The size of the DNA fragment containing the decaprenyldiphosphate synthetase gene can be determined, for example, by digesting DNA containing the gene with a suitable restriction enzyme according to a conventional method, for example, the method described in Molecular Cloning, Second Edition, followed by fractionation by agarose gel electrophoresis, and transfer and immobilization on a suitable membrane and carrying out Southern hybridization using the above DIG-labeled DNA fragment as a probe.

The DNA recovered from agarose gel can be purified, for example, by using Geneclean II kit (Bio 101 Inc., CA, USA).

The purified DNA is linked to a suitable vector which has been digested with a restriction enzyme using, for example, Ligation kit Ver. 2 (Takara Shuzo Co., Ltd.) to prepare recombinant DNA. Using the recombinant DNA, transformants containing the recombinant DNA can be obtained by transformation of *Escherichia coli*, for example, *E. coli* DH5α. Plasmid DNA carried by the transformants can be extracted according to a conventional method.

If necessary, plasmid DNA containing a DNA fragment derived from restriction enzyme-digested plasmid DNA can be obtained by digesting the plasmid DNA with a suitable restriction enzyme according to a conventional method, for example, the method described in Molecular Cloning, Second Edition and linking the obtained restriction enzyme fragments to a suitable vector after fractionation and purification.

The nucleotide sequence of the entire or a part of the resulting plasmid DNA can be determined using DyeTerminator Cycle Sequencing FS Ready Reaction Kit (Perkin-Elmer Japan) and 373A Sequencer (Perkin-Elmer Japan).

Based on the determined nucleotide sequence information, ORF and the amino acid sequence encoded thereby can be determined using a commercially available nucleotide sequence analyzing software, for example, Genetyx Mac (Software Development).

It is possible to confirm that the DNA encodes targeted decaprenyldiphosphate synthetase by comparing the determined amino acid sequence with the known amino acid sequence of decaprenyldiphosphate synthetase.

An example of DNA encoding decaprenyldiphosphate synthetase obtained according to the above method is DNA having the nucleotide sequence shown in SEQ ID NO: 1 which encodes a polypeptide having the amino acid sequence shown in SEQ ID NO: 2.

In addition to the DNA obtained above, the DNA according to the present invention also includes DNA which hybridizes to DNA consisting of the nucleotide sequence shown in SEQ ID NO: 1 under stringent conditions and which encodes a polypeptide having decaprenyldiphosphate synherase activity.

[3] Cloning of DNA Encoding p-Hydroxybenzoic Acid-Decaprenyltransferase Derived from a Microorganism Having the Ability to Form Ubiquinone-10

DNA encoding p-hydroxybenzoic acid-decaprenyltransferase of the present invention can be obtained from the microorganisms having the ability to form ubiquinone-10 described in [1] above using *Escherichia coli* in which p-hydroxybenzoic acid-octaprenyltransferase (ubiA) is defective (hereinafter referred to as ubiA-defective strain) according to the following method.

Chromosomal DNA derived from the microorganism having the ability to form ubiquinone-10 is extracted in accordance with the method described in [1](1) above and then partially digested with an appropriate restriction enzyme such as Sau 3AI. The resulting digested DNA fragments are fractionated using a conventional method such as sucrose density gradient ultracentrifugation.

2 to 8 kb DNA fragments obtained by the fractionation is linked to a plasmid vector, for example, pUC19, which has been digested with an appropriate restriction enzyme such as Bam HI, to prepare recombinant DNA.

Using the recombinant DNA, a chromosomal DNA library can be prepared by transformation of a suitable host cell, for example, *Escherichia coli* DH5α according to a conventional method (for example, the method described in Molecular Cloning, Second Edition) and obtaining transformants.

The transformants can be selected by spreading the cells on an agar medium containing a drug to which a drug resistance gene carried by the vector is resistant, for example, LB agar medium containing 100 μg/ml ampicillin, and culturing overnight at 37° C.

Plasmids carried by the transformants is extracted according to a conventional method and a ubiA-defective strain is transformed with the plasmids.

A ubiA-Defective strain is available from National Institute of Genetics, a public organization for culture collection. A ubiA-Defective strain is viable using glucose as the sole carbon source, but is not viable when succinic acid is the sole carbon source. Therefore, if plasmids extracted from the above transformants contains DNA encoding p-hydroxybenzoic acid-decaprenyltransferase, a ubiA-defective strain into which the plasmid is introduced becomes viable on an agar medium containing succinic acid as the sole carbon source. A plasmid containing DNA encoding p-hydroxybenzoic acid-decaprenyltransferase can be selected using this viability property as an index.

From transformants of the ubiA-defective strain, which are viable on an agar medium containing succinic acid as the sole carbon source, plasmid DNA carried by the transformants is extracted and the nucleotide sequence of the plasmid DNA is determined by a conventional method using, for example, DyeTerminator Cycle Sequencing FS Ready Reaction Kit (Perkin-Elmer Japan) and 373A Sequencer (Perkin-Elmer Japan).

ORF and the amino acid sequence encoded thereby can be determined from the determined nucleotide sequence using a commercially available nucleotide sequence analyzing software, for example, Genetyx Mac (Software Development).

The DNA can be determined to encode targeted p-hydroxybenzoic acid-polyprenyltransferase by comparing the determined amino acid sequence with the known amino acid sequence of p-hydroxybenzoic acid-polyprenyltransferase.

An example of the DNA encoding p-hydroxybenzoic acid-polyprenyltransferase obtained according to the above method is DNA having the nucleotide sequence shown in SEQ ID NO: 3 which encodes a polypeptide having the amino acid sequence shown in SEQ ID NO: 4.

In addition to the DNA obtained above, the DNA according to the present invention also includes DNA that hybridizes to the DNA consisting of the nucleotide sequence shown in SEQ ID NO: 3 under stringent conditions and which encodes p-hydroxybenzoic acid-polyprenyltransferase.

[4] Production of Decaprenyldiphosphate Synthetase or p-Hydroxybenzoic Acid-Decaprenyltransferase The polypeptide of the present invention can be produced by expressing DNA encoding decaprenyldiphosphate synthetase or DNA encoding p-hydroxybenzoic acid-decaprenyltransferase in a host cell using the method described in Molecular Cloning, Second Edition or Current Protocols in Molecular Biology according to, for example, the following method.

On the basis of the full length DNA of the DNA encoding decaprenyldiphosphate synthetase or p-hydroxybenzoic acid-decaprenyltransferase of the present invention, a DNA fragment of an appropriate length comprising a region encoding the polypeptide is prepared according to need.

Furthermore, DNA useful for the efficient production of the polypeptide of the present invention can be prepared, as required, by replacing a nucleotide in the nucleotide sequence of the region encoding the polypeptide so as to make a codon most suitable for the expression in a host cell.

The above DNA fragment or the full length gene is inserted downstream to a promoter region in an appropriate expression vector to construct recombinant DNA.

The recombinant DNA is introduced into a host cell suited for the expression vector.

As the host cell, any bacterial cells, yeast cells, animal cells, insect cells, plant cells, etc. that are capable of expressing the targeted gene can be used.

The expression vectors that can be employed are those capable of autonomous replication or integration into chromosome in the above host cells and comprising a promoter at a position where the transcription of the DNA encoding the polypeptide of the present invention is possible.

When a procaryotic cell such as a bacterial cell is used as the host cell, it is preferred that recombinant DNA comprising the DNA encoding the polypeptide of the present invention is capable of autonomous replication in the procaryotic cell and, at the same time, is a vector which comprises a promoter, a ribosome binding sequence, the DNA of the present invention, and a transcription termination sequence. The vector may further comprise a gene regulating the promoter.

Examples of suitable expression vectors are pBTrp2, pBTac1 and pBTac2 (all available from Boehringer Mannheim), pKK233-2 (Pharmacia), pSE280 (Invitrogen), pGEMEX-1 (Promega), pQE-8 (QIAGEN), pKYP10 (Japanese Published Unexamined Patent Application No. 110600/83), pRYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (Stratagene), pTrs30 [prepared from Escherichia coli JM109/pTrS30 (FERM BP-5407)], pTrs32 [prepared from Escherichia coli JM109/pTrS32 (FERM BP-5408)], pGHA2 [prepared from Escherichia coli IGHA2 (FERM B-400), Japanese Published Unexamined Patent Application No. 221091/85], pGKA2 [prepared from Escherichia coli IGKA2 (FERM BP-6798), Japanese Published Unexamined Patent Application No. 221091/85], pTerm2 (U.S. Pat. No. 4,686, 191, U.S. Pat. No. 4,939,094, U.S. Pat. No. 5,160,735), pSupex, pUB110, pTP5, pC194, pEG400 [J. Bacteriol., 172, 2392 (1990)], pGEX (Pharmacia), and pET system (Novagen).

As the promoter, any promoters capable of functioning in host cells can be used. For example, promoters derived from Escherichia coli or phage, such as trp promoter ($P_{trp}$), lac promoter, $P_L$ promoter, $P_R$ promoter and T7 promoter can be used. Artificially modified promoters such as a promoter in which two $P_{trp}$ are combined in tandem ($P_{trp}$×2), tac promoter, lacT7 promoter and letI promoter, etc. can also be used.

In the case of the microorganisms having the ability to produce ubiquinone-10, it is preferred to use a promoter present in a ribosomal RNA gene. An example is a promoter present in a ribosomal RNA gene derived from microorganisms of the genus Rhodobacter, specifically, a promoter comprising DNA containing of the nucleotide sequence shown in SEQ ID NO: 5.

It is preferred to use a plasmid in which the distance between the Shine-Dalgarno sequence (ribosome binding sequence) and the initiation codon is adjusted to an appropriate length (e.g., 6-18 bases).

In the case of the recombinant DNA of the present invention, the transcription termination sequence is not essential for the expression of the DNA of the invention, but it is preferred that the transcription termination sequence lie immediately downstream of the structural gene.

Examples of suitable host cells are cells of microorganisms belonging to the genera Escherichia, Serratia, Bacillus, Brevibacterium, Corynebacterium, Microbacterium, Pseudomonas, etc., specifically, those of Escherichia coli XL1-Blue, Escherichia coli XL2-Blue, Escherichia coli DH1, Escherichia coli DH5α, Escherichia coli MC1000, Escherichia coli KY3276, Escherichia coli W1485, Escherichia coli JM109, Escherichia coli HB101, Escherichia coli No. 49, Escherichia coli W3110, Escherichia coli NY49, Escherichia coli GI698, Escherichia coli TB1, Escherichia coli MP347, Escherichia coli NM522, Serratia ficaria, Serratia fonticola, Serratia liquefaciens, serratia marcescens, Bacillus subtilis, Bacillus amyloliquefacines, Brevibacterium ammoniagenes, Brevibacterium immariophilum ATCC14068, Brevibacterium saccharolyticum ATCC14066, Brevibacterium flavum ATCC14067, Brevibacterium lactofermentum ATCC13869, Corynebacterium glutamicum ATCC13032, Corynebacterium glutamicum ATCC14297, Corynebacterium acetoacidophilum ATCC13870, Microbacterium ammoniaphilum ATCC15354, Pseudomonas putida, Pseudomonas sp. D-0110, Agrobacterium radiobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warminqii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorguens, Phormidium sp. ATCC29409, Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus and Zymomonas mobilis.

Introduction of the recombinant vector can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and the methods described in Gene, 17, 107 (1982) and Molecular & General Genetics, 168, 111 (1979).

When a yeast cell is used as the host cell, YEP13 (ATCC37115), YEp24 (ATCC37051), YCp50 (ATCC37419), pHS19, pHS15, etc. can be used as the expression vector.

As the promoter, any promoters capable of functioning in yeast cells can be used. Suitable promoters include promoters of hexosekinase and other glycolytic genes, PHO5 promoter, PGK promoter, GAP promoter, ADH promoter, gal 1 promoter, gal 10 promoter, heat shock polypeptide promoter, MFα1 promoter, CUP1 promoter, etc.

Examples of suitable host cells are cells of microorganism strains belonging to the genus *Saccharomyces, Schizosaccharomyces, Kluyveromyces, Trichosporon, Schwanniomyces, Pichia* or *Candida*, specifically, the species *Saccharomyces cerevisiae, Schizosaccharomyces pombe, Kluyveromyces lactis, Trichosporon pullulans, Schwanniomyces alluvius,* or *Candida utilis.*

Introduction of the recombinant vector can be carried out by any of the methods for introducing DNA into yeast cells, for example, electroporation [Methods Enzymol., 194, 182 (1990)], the spheroplast method [Proc. Natl. Acad. Sci. USA, 75, 1929 (1978)], the lithium acetate method [J. Bacteriology, 153, 163 (1983)] and the method described in Proc. Natl. Acad. Sci. USA, 75, 1929 (1978).

When an animal cell is used as the host cell, pcDNAI, and pcDM8 (both available from Funakoshi), pAGE107 [Japanese Published unexamined Patent Application No. 22979/91; Cytotechnology, 3, 133 (1990)], pAS3-3 (Japanese Published Unexamined Patent Application No. 227075/90) pCDMB [Nature, 329, 840 (1987)], pcDNAI/Amp (Invitrogen), pREP4 (Invitrogen), pAGE103 [J. Biochem., 101, 1307 (1987)], pAGE210, etc. can be used as the expression vector.

As the promoter, any promoters capable of functioning in animal cells can be used. Suitable promoters include the promoter of IE (immediate early) gene of cytomegalovirus (CMV), SV40 early promoter, the promoter of a retrovirus, metallothionein promoter, heat shock promoter, SRα promoter, etc. The enhancer of IE gene of human CMV may be used in combination with the promoter.

Examples of suitable host cells are human-derived Namalwa cells, monkey-derived COS cells, Chinese hamster-derived CHO cells, and HBT5637 (Japanese Published Unexamined Patent Application No. 299/88).

Introduction of the recombinant vector into animal cells can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the polypeptide can be expressed by using the methods described in Current Protocols in Molecular Biology; Baculovirus Expression vectors, A Laboratory manual, W. R. Freeman and Company, New York (1992); Bio/Technology, 6, 47 (1988), etc.

That is, the recombinant gene transfer vector and a baculovirus are cotransfected into an insect cell to obtain a recombinant virus in the culture supernatant of the insect cell, and then an insect cell is infected with the recombinant virus, whereby the polypeptide can be expressed.

Examples of the gene transfer vectors suitable for use in this method are pVL1392, pVL1393 and pBlueBacIII (products of Invitrogen).

An example of the baculovirus is *Autographa californica* nuclear polyhedrosis virus, which is a virus infecting insects belonging to the family Barathra.

Examples of the insect cells are Sf9 and Sf21 which are ovarian cells of *Spodoptera frugiperda* [Baculovirus Expression Vectors, A Laboratory Manual, W. H. Freeman and Company, New York (1992)], and High 5 which is an ovarian cell of *Trichoplusia ni* (Invitrogen).

Cotransfection of the above recombinant gene transfer vector and the above baculovirus into an insect cell for the preparation of the recombinant virus can be carried out by the calcium phosphate method (Japanese Published Unexamined Parent Application No. 227075/90), lipofection [Proc. Natl. Acad. Sci. USA, 84, 7413 (1987)], etc.

When a plant cell is used as the host cell, Ti plasmid, tobacco mosaic virus vector, etc. are useful expression vectors.

As the promoter, any promoters capable of functioning in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat, and barley.

Introduction of the recombinant vector can be carried out by any of the methods for introducing DNA into plant cells, for example, the *Agrobacterium* method (Japanese Published Unexamined Patent Applications Nos. 140885/84 and 70080/85, WO94/00977), electroporation (Japanese Published Unexamined Patent Application No. 251887/85) and the method using particle gun (gene gun) (Japanese Patents Nos. 2606856 and 2517813).

The gene can be expressed either directly or as a secretory production or fusion protein expression according to the methods described in Molecular Cloning, Second Edition, etc.

When expression is effected in yeast cells, animal cells, insect cells or plant cells, sugar or sugar chain-added polypeptide can be obtained.

The polypeptide of the invention can be produced by culturing the transformant of the invention which is obtained according to the above procedure in a medium, allowing the polypeptide having decaprenyldiphosphate synthetase activity or p-hydroxybenzoic acid-decaprenyltransferase activity of the present invention to form and accumulate in the culture, and recovering the polypeptide from the culture.

Culturing of the transformant obtained above in a medium can be carried out by conventional methods for culturing a host cell of a transformant.

When the transformant of the present invention is prepared by using a procaryote such as *Escherichia coli* or a eucaryote such as yeast as the host, any of natural media and synthetic media can be used for culturing the transformant insofar as it is a medium suitable for efficient culturing of the transformant which contains carbon sources, nitrogen sources, inorganic salts, etc. which can be assimilated by the transformant used.

As the carbon sources, any carbon sources that can be assimilated by the transformant can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of various organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is carried out under aerobic conditions, for example, by shaking culture or submerged spinner culture under aeration, at 15-40° C. usually for 16 hours to 7 days. The pH is maintained preferably at 3.0-9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with a recombinant vector comprising an inducible promoter is cultured, an inducer may be added to the medium, if necessary. For example, in the case of a microorganism transformed with a recombinant vector comprising lac promoter, isopropyl-β-D-thiogalactopyranoside or the like may be added to the medium; and in the case of a microorganism transformed with a recombinant vector comprising trp promoter, indoleacrylic acid or the like may be added.

For the culturing of the transformant prepared by using an animal cell as the host cell, generally employed media such as RPMI1640 medium [The Journal of the American Medical Association, 199, 519 (1967)], Eagle's MEM [Science, 122, 501 (1952)], Dulbecco's modified MEM [Virology, 8, 396 (1959)] and 199 medium [Proceeding of the Society for the Biological Medicine, 73, 1 (1950)], media prepared by adding fetal calf serum or the like to these media, etc. can be used as the medium.

Culturing is usually carried out at pH 6-8 at 30-40° C. for 1-7 days in the presence of 5% $CO_2$.

If necessary, antibiotics such as kanamycin and penicillin may be added to the medium during the culturing.

For the culturing of the transformant prepared by using an insect cell as the host cell, generally employed media such as TNM-FH medium (Pharmingen), Sf-900 II SFM medium (Life Technologies), ExCell 400 and ExCell 405 (both JRH Biosciences) and Grace's Insect Medium [Nature, 195, 788 (1962)] can be used as the medium.

Culturing is usually carried out at pH 6-7 at 25-30° C. for 1-5 days.

If necessary, antibiotics such as gentamicin may be added to the medium during the culturing.

The transformant prepared using a plant cell as the host cell can be cultured as a cell or as a cell or organs of the plant in differentiated form. Culture media suitable for use in the culturing of the transformant include generally employed media such as Murashige-Skoog (MS) medium and White medium, and media prepared by adding phytohormones, such as auxin, cytokinin and so on, to these media.

Culturing is usually carried out at pH 5-9 at 20-40° C. for 3-60 days.

If necessary, antibiotics such as kanamycin and hygromycin may be added to the medium during the culturing.

The polypeptide of the present invention can be produced by culturing the above transformant derived from a microorganism, an animal cell or a plant cell and comprising a recombinant vector into which DNA encoding the polypeptide of the invention is incorporated according to an ordinary culturing method, allowing the polypeptide to form and accumulate, and recovering the polypeptide from the culture.

The gene can be expressed either directly or as a secretory production or fusion polypeptide expression according to the methods described in Molecular cloning, Second Edition, etc.

The polypeptide of the present invention may be produced intracellularly, secreted extracellularly or produced on outer membranes of host cells. Such production methods can be selected depending on the kind of the host cells used or on alteration of the structure of the polypeptide to be produced.

When the polypeptide of the present invention is produced in host cells or on outer membranes of host cells, it is possible to force the polypeptide to be secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published unexamined Patent Application No. 336963/93, WO94/23021, etc.

That is, extracellular secretion of the polypeptide of the invention by host cells can be caused by expressing it in the form of a polypeptide in which a signal peptide is added upstream of a polypeptide containing the active site of the polypeptide of the invention by the use of recombinant DNA techniques.

It is also possible to increase the polypeptide production by utilizing a gene amplification system using the dihydrofolate reductase gene or the like according to the method described in Japanese Published Unexamined Patent Application No. 227075/90.

Furthermore, it is possible to cause the animal cells or plant cells carrying the introduced gene to redifferentiate in order to produce an animal having the introduced gene (non-human transgenic animal) or a plant having the introduced gene (transgenic plant) and produce the polypeptide of the invention using these individuals.

When the transformant is an animal individual or plant individual, the polypeptide can be produced by raising or culturing the animal individual or plant individual in a usual manner, allowing the polypeptide to form and accumulate therein, and recovering the polypeptide from the animal or plant.

When an animal individual is used, the polypeptide of the present invention can be produced in the animal carrying the introduced gene according to known methods [American Journal of Clinical Nutrition, 63, 639S (1996); American Journal of Clinical Nutrition, 63, 627S (1996); Bio/Technology, 9, 830 (1991)].

In the case of an animal individual, the polypeptide of the present invention can be produced, for example, by raising a non-human transgenic animal carrying DNA encoding the polypeptide, allowing the polypeptide to form and accumulate in the animal, and recovering the protein from the animal. The places where the polypeptide is formed and accumulated include milk (Japanese Published Unexamined patent Application No. 309192/88), egg, etc. of the animal. As the promoter to be used, any promoters capable of functioning in an animal can be used. Preferred promoters include mammary gland cell-specific promoters such as α casein promoter, β casein promoter, β lactoglobulin promoter and whey acidic protein promoter.

In the case of a plant individual, the polypeptide of the invention can be produced, for example, by culturing a transgenic plant carrying DNA encoding the polypeptide according to known methods [Soshiki Baiyo (Tissue Culture), (1994); Soshiki Baiyo (Tissue Culture), 21 (1995); Trends in Biotechnology, 15, 45 (1997)], allowing the polypeptide to form and accumulate in the plant, and recovering the polypeptide from the plant.

Isolation and purification of the polypeptide having decaprenyldiphosphate synthetase activity or p-hydroxybenzoic acid-decaprenyltransferase activity, which has been produced by the transformant of the present invention, can be carried out by conventional methods for isolating and purifying enzymes.

For example, when the polypeptide of the present invention is expressed in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract. A purified polypeptide preparation can be obtained from the supernatant obtained by centrifuging the cell-free extract by single use or a combination of conventional methods for isolating and purifying enzymes, namely, extraction with a solvent, salting-out with ammonium sulfate, etc., desalting, precipitation with an organic solvent, anion exchange chromatography using resins such as diethylaminoethyl (DEAE)-sepharose and DIAION HPA-75 (Mitsubishi Kasei Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, electrophoresis such as isoelectric focusing, or the like.

When the polypeptide is expressed as an inclusion body in cells, the cells are similarly recovered and disrupted, followed by centrifugation to obtain the inclusion body of the polypeptide as a precipitate fraction, which is then solubilized with a protein-denaturing agent. The solubilized solution is diluted or dialyzed to reduce the concentration of the protein-denaturing agent, whereby the normal three-dimensional structure of the polypeptide is restored. After carrying out these operations, a purified polypeptide preparation can be obtained through the same isolation and purification procedures as mentioned above.

When the polypeptide of the present invention or a derivative thereof such as a polypeptide in which a sugar chain is added to the polypeptide is extracellularly secreted, the polypeptide or the derivative thereof can be recovered in the culture supernatant obtained by treating the culture using a similar centrifugation technique as described above. From the culture supernatant, purified preparation of the polypeptide can be obtained using the same isolation and purification procedures as described above.

Example of the polypeptides obtained in this manner are a polypeptide having the amino acid sequence shown in SEQ ID NO: 2 as regards the polypeptides having decaprenyldiphosphate synthetase activity, and a polypeptide having the amino acid sequence shown in SEQ ID NO: 4 regarding polypeptides having p-hydroxybenzoic acid-decaprenyltransferase activity.

In addition to the polypeptides obtained above, the polypeptides of the present invention also include polypeptides which comprise an amino acid sequence in which one or more amino acid residues are deleted, substituted or added in the amino acid sequence possessed by the above polypeptides and which have either decaprenyldiphophate synthetase activity or p-hydroxybenzoic acid-decaprenyltransferase activity.

The polypeptides of the present invention can also be produced by chemical synthetic methods such as the Fmoc method (the fluorenylmethyloxycarbonyl method) and the tBoc method (the t-butyloxycarbonyl method). Furthermore, the polypeptides can be chemically synthesized by using peptide synthesizers from Advanced ChemTech, Perkin-Elmer, Pharmacia, Protein Technology Instrument, Synthecell-vega, PerSeptive, Shimadzu Corporation, etc.

[5] Production of Ubiquinone-10

As microorganisms to be used for production of ubiquinone-10, microorganisms having the ability to form ubiquinone-10 and having one or more properties selected from the group consisting of the property wherein crtE activity is reduced or defective, the property wherein decaprenyldiphosphate synthetase activity is strengthened, and the property wherein p-hydroxybenzoic acid-decaprenyltransferase activity is strengthened are preferred.

Examples or microorganisms having the ability to form ubiquinone-10 and having the property wherein crtE activity is reduced or defective are those obtained in [1] above.

Microorganisms having the property wherein decaprenyldiphosphate synthetase activity is strengthened or those having the property wherein p-hydroxybenzoic acid-decaprenyltransferase activity is strengthened can be obtained from microorganisms having the ability to form ubiquinone-10 according to the method for introducing mutation described in [1] above. They can also be obtained by introducing DNA encoding decaprenyldiphosphate synthetase or p-hydroxybenzoic acid-decaprenyltransferase obtained by the method described in [2] and [3] above to microorganisms having the ability to form ubiquinone-10 according to the method described in [4] above.

Furthermore, microorganisms having the ability to form ubiquinone-10 and having one or more properties selected from the group consisting of the property wherein crtE activity is reduced or defective, the property wherein decaprenyldiphosphate synthetase activity is strengthened, and the property wherein p-hydroxybenzoic acid-decaprenyltransferase activity is strengthened can be obtained by the combination of the above described methods.

Ubiquinone-10 can be produced by culturing a microorganism having the ability to form ubiquinone-10 and having one or more properties selected from the group consisting of the property wherein crtE activity is reduced or defective, the property wherein decaprenyldiphosphate synthetase activity is strengthened, and the property wherein p-hydroxybenzoic acid-decaprenyltransferase activity is strengthened in a culture medium, allowing ubiquinone-10 to form and accumulate in the culture and recovering the ubiquinone-10 from the culture.

Culturing may be carried out in accordance with the culturing method described in [4] above. If necessary, aromatic compounds such as shikimic acid, chorismic acids p-hydroxybenzoic acid, etc. which are precursors of ubiquinone-10 biosynthesis and isoprenoid such as IPP, FPP, etc. may be added to the medium.

Ubiquinone-10 can be recovered from the culture by a method of recovery usually used in synthetic organic chemistry such as extraction with organic solvents, crystallization, thin layer chromatography, high performance liquid chromatography, etc.

Confirmation and quantitative analysis of the ubiquinone-10 recovered can be carried out by $^{13}$C-NMR spectrum, $^1$H-NMR spectrum, mass spectrum, high performance liquid chromatography (HPLC), the color development method, etc.

[6] Efficient Expression of Gene

The promoter present in the ribosomal RNA gene described in the polypeptide production method in [4] above is useful not only in the polypeptide production method of [4] above but in polypeptide production methods in general.

By inserting DNA encoding a polypeptide for which expression is targeted downstream to DNA comprising the nucleotide sequence of the promoter present in the ribosomal RNA gene, DNA encoding the polypeptide can be expressed efficiently, and, therefore, the polypeptide can be produced.

Useful ribosomal RNA genes are those derived from microorganisms belonging to the genus *Rhodobacter*.

An example of the promoter present in the ribosomal RNA gene is DNA having the nucleotide sequence shown in SEQ ID NO: 5.

Examples of the present invention are shown below. These examples are not to be construed as limiting the scope of the invention. Unless otherwise referred to, the recombinant DNA experiments shown in the following examples were carried out using the method described in Molecular Cloning, Second Edition (hereinafter referred to as "a conventional method").

BEST MODES FOR CARRYING OUT THE INVENTION

Example 1

Construction of a Microorganism Strain Wherein crtE is Reduced or Defective (1) Preparation of DNA Comprising DNA Encoding crtE Oligodeoxyribonucleotides having the nucleotide sequence shown in SEQ ID NO: 7 or 8 were synthesized utilizing the previously published nucleotide sequence of a carotenoid biosynthetase gene cluster containing crtE of *R. sphaeroides* [J. Bacteriology, 177, 2064-2073 (1995)] using a DNA synthesizer. They were used as a set of primers in PCR.

Chromosomal DNA of *R. sphaeroides* KY4113 (FERM BP-4675) was cultured overnight using 50 ml of LB medium [1% Bacto Tryptone (Difco), 0.5% Bacto Yeast Extract (Difco), 5% NaCl] and cells were recovered.

After being subjected to freezing and thawing once, the cells were suspended in 10 ml of a buffer [50 mmol/l Tris HCl, 20 mmol/l EDTA (pH 8.0)] containing 0.5 mg/ml lysozyme and incubated at 37° C. for 3 hours.

To the suspension were added 1 ml of proteinase K (1 mg/ml) and 100 µl of 10% SDS and the mixture was incubated at 50° C. for 3 hours. Then the mixture was allowed to restore to room temperature and subjected to extraction with phenol/chloroform, followed by precipitation with ethanol, whereby the chromosomal DNA was purified.

PCR amplification was carried out using a set of primers having the nucleotide sequence shown in SEQ ID NO: 7 or 8 synthesized above with the chromosomal DNA as a template.

PCR was carried out by 30 cycles, one cycle consisting of reaction at 98° C. for 20 seconds, and reaction at 68° C. for 5 minutes, using TaKaRa LA-Taq.

A targeted, PCR-amplified about 2.5 kb DNA fragment was subjected to blunting and phosphorylation and inserted to the Sma I site of a plasmid vector, pUC19, to prepare a recombinant plasmid.

*Escherichia coli* DH5α (Toyobo) was transformed with the recombinant plasmid and spread on LB agar medium containing 100 µg/ml ampicillin to obtain transformants.

A plasmid was extracted from the transformant and the nucleotide sequence of the DNA inserted to the Sma I site of the plasmid was determined.

Based on the determined nucleotide sequence, it was confirmed that the DNA contains parts of ORFs which are present in upstream and downstream crtE.

The plasmid was named pUCRTE-1.

Analysis of the restriction enzyme sites of pUCRTE-1 revealed that Bal I and Stu I are present, one each, only inside crtE and that the distance between both restriction enzyme sites is about 450 bp. Thus, the present inventors considered it was possible to cause GGPP synthetase activity of crtE to be reduced or become defective by deleting this region of about 450 bp and conducted the following experiment.

pUCRTE-1 was subjected to double digestion with Bal I and Stu I and its complete digestion was confirmed by agarose gel electrophoresis. Then an about 4.6 kb DNA fragment was separated and purified using QIAEX II (Qiagen). The purified DNA fragment was subjected to blunting and dephosphorylation.

To facilitate the selection of crtE-defective strains, a plasmid carrying a kanamycin resistance gene inserted into the obtained DNA was prepared according to the following procedure.

The kanamycin resistance gene derived from Tn5 and the glnB promoter region derived from *R. sphaeroides* [Microbiology, 140, 2143-2151 (1994)] were each isolated by PCR and ligated together, followed by blunting and phosphorylation, which was then ligated to the 4.6 kb fragment previously prepared, whereby a recombinant plasmid was prepared.

*Escherichia coli* DH5α was transformed with the recombinant plasmid and then spread on LB agar medium containing 100 µg/ml ampicillin to obtain transformants.

A Plasmid was extracted from the transformants and was confirmed to carry the kanamycin resistance gene inserted into the site where crtE was deleted.

The plasmid was named pUΔCRTE-1.

(2) Preparation of a Strain in which GGPP Synthetase Activity is Reduced or Defective pUΔCRTE-1 obtained in (1) above was introduced into *R. sphaeroides* KY4113 according to the following method.

KY4113 was inoculated into LB liquid medium and cultured until its logarithmic growth phase. After the culturing, cells were recovered by centrifugation. The cells were washed twice with an aqueous solution containing 10% glycerol and 1 mmol/l HEPES to remove the medium components to the utmost.

The washed cells and 10 µg of pUΔCRTE-1 were placed in a 0.1 cm width cuvette for electroporation (Bio-Rad) and electroporation was carried out under the conditions of 400Ω, 25 µF, and 12.5 kv/cm using Gene Pulser (Bio-Rad), to introduce pUΔCRTE-1 into the cells.

The resulting cells were cultured at 30° C. for 3 hours using SOC medium (a medium prepared by adding 20 g of Bacto Tryptone (Difco), 5 g of Bacto Yeast Extract (Difco), 2 ml of 5 mol/l NaCl, and 1.25 ml of 2 mol/l KCl together, to which water is added to prepare a solution of 990 ml, autoclaving the solution, and adding 10 ml of 2 mol/l glucose solution to the solution). The obtained culture was spread on LB agar medium containing 10 µg/ml kanamycin and cultured at 30° C. for 3 days.

As a result of the culturing, 18 colonies were formed of which 11 formed red carotenoid pigment as in the case of the wild strain and 7 lacked carotenoid productivity.

After culturing each of the colonies, chromosomal DNA was extracted and analyzed.

It was revealed that the 7 strains that lost carotenoid productivity carried the kanamycin resistance gene inserted within the crtE gene on the chromosome.

It was considered that pUΔCRTE-1 introduced by electroporation underwent two-site crossing-over at regions upstream and downstream the kanamycin resistance gene with the homologous regions of chromosome and was inserted, which caused deletion of the crtE gene and, therefore, loss of enzymatic activity encoded by the crtE gene (GGPP synthetase activity) so that the strains could not produce carotenoid any more.

The ampicillin resistance gene carried by pUΔCRTE-1 was not introduced into the chromosomal DNA of these strains and DNA derived from the vector was not incorporated into their chromosomal DNA.

In the 11 strains which maintained carotenoid productivity, both ampicillin resistance gene and kanamycin resistance gene were confirmed on the chromosome and, thus, they were revealed to contain the normal crtE, with the sequence of pUΔCRTE-1 inserted to the chromosomal DNA by one-site crossing-over.

The crtE-defective strains thus obtained were named KY4113ΔcrtE-1 to 7.

The KY4113ΔcrtE-1 to 7 strains were confirmed to be crtE-defective strains as their carotenoid productivity was restored by introducing the normal crtE gene into them. That is, a recombinant plasmid carrying the normal crtE gene inserted to a wide host range vector, pEG400, [J. Bacteriology, 172, 2392 (1990)] was prepared and introduced into these strains, and it was confirmed that they produce carotenoid pigment.

Example 2

Production of Ubiquinone-10 by crtE-Defective Strains

One platinum loop of each of KY4113ΔcrtE-1 to 7 strains obtained in Example 1 was inoculated into 5 ml of a seed medium [2% glucose, 1% peptone, 1% yeast extract, 0.5% NaCl (pH 7.2 adjusted by NaOH)] in a test tube and cultured at 30° C. for 24 hours.

The resulting culture (0.5 ml) was inoculated into 5 ml of a ubiquinone-10 producing medium [prepared by adjusting a medium containing 4% molasses, 2.7% glucose, 4% corn steep liquor, 0.8% ammonium sulfate, 0.05% potassium dihydrogenphosphate, 0.05% dipotassium hydrogenphosphate, 0.025% magnesium sulfate.7 hydrate, 3 mg/l ferrous sulfate.7 hydrate, 8 mg/l thiamine, 8 mg/l nicotinic acid, and 1 ml/l trace elements (a solution containing 88 mg/l $Na_2B_4O_7.10H_2O$, 37 mg/l $(NH_4)_6Mo_7O_{24}.4H_2O$, 8.8 mg/l $ZnSO_4.7H_2O$, 270 mg/l $CuSO_4.5H_2O$, 7.2 mg/l $MnCl_2.4H_2O$, and 970 mg/l $FeCl_3.6H_2O$) to pH 9, adding 1% calcium carbonate thereto, and autoclaving the resulting mixture] in a test tube and cultured with shaking at 30° C. for 5 days.

After the completion of culturing, 300 μl of 2-butanol and 300 μl of glass beads were added to 300 μl of the broth and extraction with solvent was carried out while disrupting the cells with Multi Beads Shocker MB-200 (Yasui Kiki) for 5 minutes.

The liquid extract was separated by centrifugation to recover a 2-butanol layer. The production amount of ubiquinone-10 in the 2-butanol layer was calculated by carrying out high performance liquid chromatography (HPLC) under the following conditions:

Conditions for HPLC
Apparatus: LC-10A (Shimadzu Corporation)
Column: Develosil ODS-HG-5 (Nomura Kagaku)
Moving phase: methanol:n-hexane=8:2
Velocity: 1 ml/mm.
Measured wavelength: 275 nm
The results are shown in Table 1.

TABLE 1

| | Growth (OD660) | Titer of ubiquinone-10 (mg/l) | Content (Titer/growth) |
|---|---|---|---|
| KY4113 | 23.6 | 90.8 | 3.9 |
| KY4113ΔcrtE-1 | 21.7 | 127.3 | 5.9 |
| KY4113ΔcrtE-2 | 21.4 | 120.6 | 5.6 |
| KY4113ΔcrtE-3 | 21.9 | 112.2 | 5.1 |
| KY4113ΔcrtE-4 | 21.8 | 120.1 | 5.5 |
| KY4113ΔcrtE-5 | 20.1 | 112.6 | 5.6 |
| KY4113ΔcrtE-6 | 20.9 | 128.2 | 6.1 |
| KY4113ΔcrtE-7 | 24.7 | 159.5 | 6.5 |

The production amount of ubiquinone-10 was significantly higher for KY4113ΔcrtE-1 to 7 strains as compared with KY4113 used as a control. That is, it was found for the first time that ubiquinone-10 productivity could be improved by causing crtE activity of *R. sphaeroides* to become defective.

It was also found that gene disruption by electroporation using a DNA fragment into which the deletion was introduced was a very excellent method.

According to this method, no special vector or host cell required by the conjugation method is necessary, and any vectors that are incapable of autonomous replication in photosynthetic bacteria, for example, pUC19 as well as straight chain DNA such as PCR amplified fragments can be utilized.

It is considered that the amount of ubiquinone-10 accumulation increased because FPP that has previously flown toward carotenoid or bacteriochlorophyll side chain via crtE gene products now flows toward the ubiquinone biosynthetic pathway according to this method. The mutants obtained according to the present invention have growth characteristics and nutrition auxotrophy similar to those possessed by the parent strain because no mutation is newly introduced in addition to the crtE mutation.

Example 3

Cloning of the Decaprenyldiphosphate Synthetase Gene (DPPS) from a Photosynthetic Bacterium *R. sphaeroides*

The present inventors considered that ubiquinone-10 could be produced efficiently by strengthening the ubiquinone biosynthetic pathway and attempted to obtain a gene participating in the ubiquinone-10 biosynthetic system.

As the gene, first, we noted the decaprenyldiphosphate synthetase gene (DPPS).

DPPS is very likely to efficiently draw FPP which is presumed to become excessive by the defectiveness of crtE toward the ubiquinone biosynthetic pathway, therefore, it is possible that a strain obtained by introducing the DPPS into a crtE-defective strain produces ubiquinone-10 more efficiently than a strain in which the DPPS is introduced into a crtE non-defective strain.

To obtain the decaprenyldiphosphate synthetase gene derived from *R. sphaeroides*, the degenerate PCR method [Bio Experiments Illustrated (3), Shujunsha (199)] was carried out.

Search for the known decaprenyldiphosphate synthetase gene derived from other biological species was conducted for the DNA database of Genbank. As a result, the gene was confirmed to be present in *B. subtilis, B. stearothermophilus*, E. coli, G. suboxydans, H. influenzae, H. pylori, R. capsulatus, S. serevisiae, S. pombe, Synechocystis sp. PCC6803, etc. Their sequences were compared and highly conserved amino acid sequences were selected. Nucleotide sequences corresponding to the amino acid sequences selected were designed taking the frequency of the codon usage of R. sphaeroides used into consideration and a DNA fragment having the nucleotide sequence shown in SEQ ID NO: 9 was synthesized as the sense primer and a DNA fragment having the nucleotide sequence shown in SEQ ID NO: 10 as the antisense primer by using a DNA synthesizer.

PCR was carried out using the above primers and EXPAND™ High-Fidelity PCR System (Boehringer Mannheim) with chromosomal DNA of R. sphaeroides KY4 113 (FERM P-4675) as a template in DNA Thermal Cycler (Perkin-Elmer Japan).

PCR was carried out by 35 cycles, one cycle consisting of reaction at 94° C. for 40 seconds, reaction at 60° C. for 40 seconds and reaction at 72° C. for 45 seconds.

An about 400 bp amplified DNA fragment was obtained by PCR.

The nucleotide sequence of the DNA fragment was determined and the DNA fragment was confirmed to have a high homology to the known polyprenyldiphosphate synthetase. The DNA fragment was purified and subjected to DIG-labeling using DIG DNA Labeling Kit (Boehringer Mannheim).

To obtain the full length decaprenyldiphosphate synthetase gene of R. sphaeroides KY4113, a genomic DNA library of the KY4113 strain was prepared according to the following method.

KY4113 was cultured on LB medium overnight and chromosomal DNA was extracted. The extract was partially digested with Sau 3AI and 4 to 6 kb DNA fragments were purified by sucrose density gradient ultracentrifugation.

The DNA fragments and a vector, pUC19, digested with Bam HI were subjected to ligation using Ligation Pack (Nippon Gene) to prepare recombinant plasmids.

E. coli DH5α was transformed with the obtained recombinat plasmid and spread on LB plate containing 100 g/ml ampicillin, whereby about 10000 recombinant strains were obtained.

The recombinant strains were subjected to screening according to the colony hybridization method by using the DIG-labeled DNA fragment obtained above as a probe and 5 colonies that hybridize to the DIG-labeled DNA fragment were obtained.

A plasmid was extracted by a conventional method from the strains derived from the colonies and digested with a restriction enzyme and the size of the DNA fragments inserted were compared.

The above 5 strains contained the inserted DNA fragments of the same size and the DNA fragments were revealed to contain a common sequence through sequencing.

ORF encoding 333 amino acids that have a high homology to the polyprenyldiphosphate synthetase gene of other biological species was present in the sequence.

The nucleotide sequence is shown in SEQ ID NO: 1 and the amino acid sequence in SEQ ID NO: 2.

Example 4

Production of Ubiquinone-10 by Recombinant R. sphaeroides

A recombinant plasmid in which an about 4 kb DNA fragment containing the DPPS gene cloned in Example 3 was linked to a wide host range vector, pEG400, was prepared. The plasmid was named pEGDPPS-1.

pEGDPPS-1 and pEG400 as a control were introduced into KY4113 and KY4113ΔcrtE-1 obtained in Example 1, respectively, by electroporation. Electroporation was carried out under the conditions of 400Ω, 25 µF, and 12.5 kv/cm using Gene Pulser (Bio-Rad).

After carrying out electroporation, the cells carrying the introduced plasmid were cultured at 30° C. for 3 hours using SOC medium and then spread on LB agar medium containing 100 µg/ml spectinomycin, followed by culturing at 30° C. for 3 days.

Transformants grown are cultured, plasmid was extracted from the cells and each strain was confirmed to contain the introduced plasmid.

The transformants obtained were named KY4113/pEGDPPS-1, KY4113/pEG400, KY4113ΔcrtE-1/pEGDPPS-1, and KY4113ΔcrtE-1/pEG400, respectively.

One platinum loop of each of the transformants was inoculated into 5 ml of a seed medium containing 100 µg/ml spectinomycin in a test tube and cultured at 30° C. for 24 hours.

0.5 ml of the resulting culture was added to 5 ml of a ubiquinone-10 production medium containing 100 µg/ml spectinomycin in a test tube and cultured at 30° C. for 5 days with shaking.

After the completion of culturing, ubiquinone-10 was extracted from the culture in accordance with the method described in Example 2 and the production amount of ubiquinone-10 was calculated by quantitative analysis using HPLC.

The results are shown in Table 2.

TABLE 2

|  | Growth (OD660) | Titer of ubiquinone-10 (mg/l) | Content (Titer/growth) |
| --- | --- | --- | --- |
| KY4113/pEG400 | 26.8 | 72.5 | 2.7 |
| KY4113/pEGDPPS-1 | 26.98 | 119.9 | 4.4 |
| KY4113ΔcrtE-1/pEG400 | 31.16 | 119.2 | 3.8 |
| KY4113ΔcrtE-1/pEGDPPS-1 | 29.56 | 151.1 (170.9) | 5.1 (5.8) |

The values in the parentheses include ubiquinone-10 precursors.

The production amount of ubiquinone-10 was significantly higher for KY4113/pEGDPPS-1 as compared with KY4113/pEG400 used as a control. Furthermore, higher ubiquinone-10 productivity was shown by using KY4113ΔcrtE-1 as the host.

From these results, it was found that the decaprenyldiphosphate synthesis is rate limiting in ubiquinone-10 biosynthesis and that pool of FPP, a substrate for decaprenyldiphosphate synthetase, increases by the deletion of the crtE gene.

An unknown substance was detected in KY4113ΔcrtE-1/pEGDPPS-1 by HPLC analysis, which was not observed in other recombinant strains. So, the substance was isolated and purified for analyses by absorption spectrum and mass spectrum.

As a result of the analyses, the unknown substance was revealed to be an intermediate for the biosynthesis of ubiquinone-10. It was presumed that as DPPS activity was strengthened, a new rate limiting point was present or arose in the biosynthesis pathway downstream the decaprenyldiphophate synthesis. These findings have been found for the first time by the present inventors.

Example 5

Search for Strong Promoters

From the results of Example 4, the decaprenyldiphosphate synthesis was revealed to be rate limiting in ubiquinone-10 biosynthesis. Therefore, it was presumed that the productivity of ubiquinone-10 would be further improved if DPPS could be forced to express by using a stronger promoter.

With regard to promoters of microorganisms having the ability to form ubiquinone-10, there is a finding concerning a promoter that highly expresses under unaerobic photosynthetic culturing conditions but is almost no finding under aerobic heterotrophic culturing conditions.

As to the promoter highly expressing under unaerobic photosynthetic culturing conditions, there is a report on unaerobic culturing of R. capsulatus into which recombinant plasmid constructed by using a promoter of the R. capsulatus-derived glutamine synthetase gene (glnB) was introduced (Japanese Published Unexamined Patent Application No. 107789/96).

Based on the report, we constructed recombinant plasmid pEGglnB-DPPS-1 in which an upstream sequence of the glnB gene [Microbiology, 140, 2143-2151 (1994)] derived from R. sphaeroides was linked upstream to DNA encoding DPPS and prepared a strain in which the recombinant plasmid was introduced into R. sphaeroides KY4113. However, ubiquinone-10 productivity could not be improved.

Through the search newly conducted for strongly expressing promoters, an rRNA promoter was found to be effective.

The sequence of rRNA gene of R. sphaeroides has already been published and 3 kinds, namely, rrnA, rrnB, and rrnC have been known [Nucleic Acids Res., 18, 7267-7277 (1990)]. The sequence upstream the rRNA gene was subjected to PCR cloning by the following method.

Based on the known sequence information, for the cloning of the upstream rrnC gene, for example, a DNA fragment having the nucleotide sequence shown in SEQ ID NO: 11 was designed as the sense primer and a DNA fragment having the nucleotide sequence shown in SEQ ID NO: 12 as the antisense primer. In so designing, the restriction enzyme Xba I site was added to the sense primer and the restriction enzyme Kpn I site to the antisense primer and in addition, a ribosomal binding site was designed for the antisense primer.

PCR was carried out using the above primers and EXPAND™ High-Fidelity PCR System (Boehringer Mannheim) with chromosomal DNA of R. sphaeroides KY4113 (FERM P-4675) as a template in DNA Thermal Cycler (Perkin-Elmer Japan).

PCR was carried out by 30 cycles, one cycle consisting of reaction at 94° C. for 40 seconds, reaction at 60° C. for 40 seconds and reaction at 72° C. for 45 seconds.

An about 200 bp amplified DNA fragment was obtained by PCR. The nucleotide sequence of the DNA fragment was determined and the DNA fragment was confirmed to be the targeted one.

A recombinant plasmid in which the DNA fragment linked upstream to a kanamycin-resistant gene was inserted into a wide host range vector, pEG400, was prepared.

The recombinant plasmid was introduced into R. sphaeroides KY4113 by electroporation and the cells of the resulting strain was spread on LB agar medium containing 100 µg/l spectinomycin and cultured at 30° C. for 3 days to obtain transformants.

The transformants were tested on LB agar medium containing kanamycin.

The transformants into which a control pEG400 was introduced did not grow on the medium containing 10 µg/l kanamycin, but those into which the recombinant plasmid having the DNA upstream rrnC was introduced was viable even in the presence of 100 µg/l kanamycin. Thus, it was confirmed that the upstream sequence of rRNA obtained above has a strong promoter activity. Expression of DPPS gene was attempted using the promoter according to the following method.

On the basis of the information on the sequence of the DPPS gene derived from R. sphaeroides confirmed in Example 3, the ORF region was amplified by PCR. DNA in which the restriction enzyme Kpn I site (5' ccggtacc 3') is added to a 5'-terminal of DNA having the nucleotide sequence of nucleotides 1-24 in SEQ ID NO: 1 was used as the sense primer and DNA wherein additional sequence (5' cc 3')-restriction enzyme Eco RI site (5' gaattc 3')-initiation/termination codon (5' tca 3') was added to a 5'-terminal of the complementary sequence of the nucleotide sequence of nucleotides 979-990 in SEQ ID NO: 1 was used as the antisense primer. PCR was carried out in accordance with the method of Example 3 using a set of these primers.

After digesting both terminals of the amplified DNA fragment obtained by PCR with Kpn I and Eco RI, the DNA fragment was purified by a conventional method.

The PCR amplified DNA on the promoter region was digested with Xba I and Kpn I and purified.

A recombinant plasmid was obtained by ligating the above two DNA fragments to an Xba I and Eco RI-double digestion product of a wide host range vector, pEG400, the nucleotide sequence of the DNA inserted to the recombinant plasmid was determined and the recombinant plasmid was confirmed to carry the DPPS gene linked directly below the upstream sequence of the targeted rrnC. The recombinant plasmid was named pEGrrnC-DPPS-1.

Furthermore, plasmid, pEGglnB-DPPS-1 was constructed in the similar manner so that the expression of the DPPS gene is enabled using the upstream sequence of glnB already reported.

Example 6

Production of Ubiquinone-10 Using Transformants Carrying Plasmid Highly Expressing the Decaprenyldiphosphate Synthetase Gene The recombinant plasmid pEGrrnC-DPPS1 and also pEG400, pEGDPPS-1 and pEGglnB-DPPS1 as controls were introduced into KY4113 by electoporation.

The cells into which the plasmid was introduced were cultured at 30° C. for 3 hours using SOC medium. The obtained culture was spread on LB agar medium containing 100 µg/ml spectinomycin and cultured at 30° C. for 3 days.

Plasmid was extracted from the cells obtained by culturing the transformants. It was confirmed that the transformants contained the plasmid introduced thereinto.

The transformants obtained according to the above method were named KY4113/pEGrrnC-DPPS1, KY4113/pEG400, KY4113/pEGDPPS-1, and KY4113/pEGglnB-DPP1, respectively.

One platinum loop of each of the transformants was inoculated into 5 ml of a seed medium containing 100 µg/ml spectinomycin in a rest tube and cultured at 30° C. for 24 hours.

The resulting cultures were added, each 0.5 ml, to 5 ml of a ubiquinone-10 production medium containing 100 µg/ml spectinomycin in a test tube, respectively, and cultured at 30° C. for 5 days with shaking.

After the completion of culturing, ubiquinone-10 was recovered from a culture according to the method described in Example 2 above and the production amount of ubiquinone-10 was calculated by quantitative analysis by using HPLC.

The results are shown in Table 3.

TABLE 3

|  | Growth (OD660) | Titer of ubiquinone-10 (mg/l) | Content (Titer/growth) |
|---|---|---|---|
| KY4113/pEG400 | 27.5 | 83.7 | 3.0 |
| KY4113/pEGDPPS-1 | 29.9 | 132.9 | 4.4 |
| KY4113/pEGglnB-DPPS-1 | 29.5 | 117.1 | 4.0 |
| KY4113/pEGrrnC-DPPS-1 | 28.6 | 188.8 | 6.6 |

From the fact that the production amount of ubiquinone-10 was the highest in KY4113/pEGrrnC-DPPS-1, it was found that ubiquinone-10 productivity could be very efficiently improved by strengthening the expression of decaprenyl-diphosphate synthetase. Also it was revealed that the promoter derived from rRNA was much stronger than the glnB promoter so far known and useful for the production of ubiquinone-10.

Example 7

Cloning of the p-Hydroxybenzoic Acid-Decaprenyltransferase Gene Derived from *R. sphaeroides*

Chromosomal DNA of *R. sphaeroides* FERM BP-4675 was obtained according to the method described in Example 1 (1) and 200 µg of the chromosomal DNA obtained was partially digested with Sau 3AI.

The resulting partially digested DNA fragments were fractionated by sucrose density gradient ultracentrifugation and 2-8 kb DNA fragments were ligated to a plasmid vector, pUC19, digested with Bam HI. *E. coli* DH5α was transformed by a conventional method with the ligation product and the resulting cells were spread on LB agar medium containing 100 µg/ml ampicillin and cultured at 37° C. overnight to prepare a genomic DNA library consisting of about 50,000 transformants.

A plasmid carried by the transformants constituting the genomic DNA library was extracted according to a conventional method and ubiA-defective strains, that is, strains in which p-hydroxybenzoic acid transferase (ubiA) is defective, were transformed with the plasmid.

The transformants obtained were spread on M9 minimal medium (a medium prepared by autoclaving a solution containing 6 g/l Na$_2$HPO$_4$, 3 g/l KH$_2$PO$_4$, 5 g/l NaCl, 1 g/l Na$_4$Cl, and 1.8% Bacto Agar and then adding thereto 1 mmol/l MgSO$_4$, 4 mg of vitamin B1, 0.4% succinic acid, and 50 mg of methionine that were separately autoclaved) containing succinic acid as the sole carbon source and cultured.

A plasmid was extracted from one transformant strain grown on M9 minimal medium containing succinic acid as the sole carbon source according to a conventional method, and the plasmid was introduced into the ubiA-defective strain once again to confirm that the ubiA-defective strain was given the ability to grow when succinic acid is the sole carbon source by the plasmid.

The nucleotide sequence of the DNA fragment inserted to the plasmid was determined using 373A sequencer (Perkin-Elmer Japan).

The determined nucleotide sequence was analyzed with Genetyx Mac (Software Development) to confirm that ORF encoding a polypeptide that is highly homologous to the known amino acid sequence of p-hydroxybenzoic acid-polyprenyltransferase was present.

Example 8

Production of Ubiquinone-10 by Transformants Containing Plasmid Highly Expressing the p-Hydroxybenzoic Acid-Decaprenyltransferase Gene Primers for PCR were designed on the basis of the sequence information found in Example 7. The sense primer and antisense primer used were the primer in which the restriction enzyme Kpn I-recognizing sequence is added to a 5'-terminal for the former and the primer in which the restriction enzyme Eco RI-recognizing sequence was added to a 5'-terminal for the latter.

DNA encoding p-hydroxybenzoic acid-decaprenyltransferase was amplified by PCR using chromosomal DNA of *R. sphaeroides* KY4113 (FERM BP-4675) as a template.

Both terminals of the resulting amplified DNA fragment were digested with Kpn I and Eco and the DNA fragment was purified by a conventional method.

Two DNA fragments, that is, the DNA fragment obtained above and the rrnC-derived promoter DNA containing Xba I- and Kpn I-recognizing sequences at respective terminals obtained in Example 5, were ligated to a Xba I and Eco RI-double digestion product of a wide host range vector, pEG400, to obtain recombinant plasmid.

*E. coli* DH5α was transformed with the recombinant plasmid and then plasmid carried by the resulting transformants was extracted by a conventional method. The nucleotide sequence of the DNA fragment inserted to the plasmid was determined.

By analyzing the nucleotide sequence of the inserted DNA fragment, the recombinant plasmid was confirmed to carry DNA encoding p-hydroxybenzoic acid-decaprenyltransferase linked directly downstream to the promoter derived from rrnC. The plasmid was named pEGrrnC-ubiA1.

A plasmid in which DNA encoding p-hydroxybenzoic acid-decaprenyltransferase is linked downstream to a glnB promoter derived from KY4113 was constructed in the similar manner and the plasmid was named pEGglnB-ubiA1.

Plasmid pEGrrnC-ubiA1 and pEGglnB-ubiA1, and pEG400 as a control were introduced into KY4113 by electroporation.

The cells into which the plasmid was introduced were cultured at 30° C. for 3 hours using SOC medium. The resulting culture was spread on LB agar medium containing 100 µg/ml spectinomycin and cultured at 30° C. for 3 days.

Transformants grown were cultured and plasmid was extracted from the resulting cells. It was confirmed that the transformants contained the plasmid introduced thereinto.

The transformants obtained in this manner were named KY4113/pEGrrnC-ubiA1, KY4113/pEGglnB-ubiA1 and KY4113/pEG400, respectively.

One platinum loop of the cells of each of the obtained strains was inoculated into 5 ml of a seed medium containing 100 µg/ml spectinomycin in a test tube and cultured at 30° C. for 24 hours.

The resulting cultures were added to 5 ml of a ubiquinone-10 production medium containing 100 µg/ml spectinomycin in a test tube in an amount of 0.5 ml, respectively, and cultured at 30° C. for 5 days with shaking.

After the completion of culturing, ubiquinone-10 was recovered from a culture in accordance with the method described in Example 2 and the production amount of ubiquinone-10 was calculated by quantitative analysis using HPLC.

The results are shown in Table 4.

TABLE 4

|  | Growth (OD660) | Titer of ubiquinone-10 (mg/l) | Content (Titer/ growth) |
|---|---|---|---|
| KY4113/pEG400 | 23.42 | 58.3 | 2.5 |
|  | 24.22 | 63.6 | 2.6 |
| KY4113/ pEGrrnC-ubiA1 | 23.14 | 85.4 | 3.7 |
|  | 22.8 | 81.8 | 3.6 |
| KY4113/ pEGglnB-ubiA1 | 24.2 | 78.6 | 3.2 |
|  | 22.26 | 74.7 | 3.4 |

The production amount of ubiquinone-10 was significantly higher with KY4113/pEGglnB-ubiA1 and KY4113/pEGrrnC-ubiA1 as compared with the control KY4113/pEG400. Among the transformants compared, KY4113/pEGrrnC-ubiA1 showed the highest ubiquinone-10 productivity.

INDUSTRIAL APPLICABILITY

According to the present invention, a process for producing ubiquinone-10 which is useful for the improvement of the conditions of heart disease and as a substance having an antioxidative function, DNA and a polypeptide useful for the production process, microorganisms useful for the production, method for expressing a gene in the microorganisms, and a method for breeding the microorganisms can be offered.

[Sequence Listing Free Text]

| SEQ ID NO: 7 | Description of the artificial sequence: synthetic DNA |
|---|---|
| SEQ ID NO: 8 | Description of the artificial sequence: synthetic DNA |
| SEQ ID NO: 9 | Description of the artificial sequence: synthetic DNA |
| SEQ ID NO: 10 | Description of the artificial sequence: synthetic DNA |
| SEQ ID NO: 11 | Description of the artificial sequence: synthetic DNA |
| SEQ ID NO: 12 | Description of the artificial sequence: synthetic DNA |

The invention claimed is:

1. A process for producing ubiquinone-10, which comprises:

obtaining a microorganism belonging to the species *Rhodobacter sphaeroides* having the ability to form ubiquinone-10 and having a disrupted chromosomal geranylgeranyl pyrophosphate synthetase gene, wherein geranylgeranyl pyrophosphate synthetase activity is defective;

transforming the microorganism with a DNA selected from the group consisting of:

(a) a DNA encoding a polypeptide comprising an amino acid sequence having at least 95% homology to the amino acid sequence shown in SEQ ID NO:2 and having decaprenyldiphosphate synthetase activity, and (b) a DNA encoding a polypeptide comprising an amino acid sequence having at least 95% homology to the amino acid sequence shown in SEQ ID NO:4 and having p-hydroxybenzoic acid-decaprenyltransferase activity;

culturing the transformed microorganism in culture;

allowing ubiquinone-10 to form and accumulate in the culture; and recovering ubiquinone-10 from the culture.

2. The process according to claim 1, wherein the chromosomal geranylgeranyl pyrophosphate synthetase gene is a DNA comprising the nucleotide sequence of SEQ ID NO: 6.

3. A process according to claim 1 or 2, wherein the disrupted chromosomal geranylgeranyl pyrophosphate synthetase gene is obtained by homologous recombination.

* * * * *

UNITED STATES PATENT AND TRADEMARK OFFICE
CERTIFICATE OF CORRECTION

| | |
|---|---|
| PATENT NO. | : 7,422,878 B1 |
| APPLICATION NO. | : 10/110393 |
| DATED | : September 9, 2008 |
| INVENTOR(S) | : Koichiro Miyake et al. |

It is certified that error appears in the above-identified patent and that said Letters Patent is hereby corrected as shown below:

TITLE PAGE AT (30) FOREIGN APPLICATION PRIORITY DATA

"11/291959" should read --11-291959--.

TITLE PAGE AT (56) U.S. PATENT DOCUMENTS

Insert: --6,103,488   8/2001   Matsuda et al. ............... 435/41--.

TITLE PAGE AT (56) OTHER PUBLICATIONS

Insert: --Dryden, et al., "Identification of *cis*-Acting Regulatory Regions Upstream of the rRNA Operons of *Rhodobacter sphaeroides*", *Journal of Bacteriology*, Vol. 175, No. 20 (1993), pages 6392-6402.--;

--Yoshida, et al., "Production of ubiquinone-10 using bacteria", *The Journal of General and Applied Microbiology*, Vol. 44, No. 1 (1998), pages 19-26--; and --EMBL/GenBank/DDBJ, Accession No. AJ010302, 3/11/1999--.

COLUMN 2

Line 7, "WILLY" should read --WILEY--; and
Line 32, "on" should read --on the--.

COLUMN 3

Line 1, "have" should read --has--; and
Line 55, "diphos-phate" should read --diphosphate--.

COLUMN 4

Line 15, "geranylgeranyltransferase" should read --geranylgeranyl pyrophosphate synthetase--.

COLUMN 6

Line 23, "carried" should read --is carried--.

UNITED STATES PATENT AND TRADEMARK OFFICE
CERTIFICATE OF CORRECTION

| | | |
|---|---|---|
| PATENT NO. | : 7,422,878 B1 | |
| APPLICATION NO. | : 10/110393 | |
| DATED | : September 9, 2008 | |
| INVENTOR(S) | : Koichiro Miyake et al. | |

It is certified that error appears in the above-identified patent and that said Letters Patent is hereby corrected as shown below:

COLUMN 7

Line 43, "ing" (first occurrence) should read --es--.

COLUMN 9

Line 40, "minute" should read --minutes--.

COLUMN 10

Line 41, "have" should read --has--;
    Line 63, "on" should read --on its--; and
    Line 64, "on" should read --on its--.

COLUMN 11

Line 60, "*Hericobacter*" should read --*Helicobacter*--; and
    Line 61, "*serevisiae*" should read --*cerevisiae*--.

COLUMN 13

Line 66, "syntherase" should read --synthetase--.

COLUMN 14

Line 32, "is" should read --are--; and
    Line 40, "contains" should read --contain--.

COLUMN 15

Line 35, "into" should read --into the--;
    Line 39, "procaryotic" should read --prokaryotic--;
    Line 42, "procaryotic" should read --prokaryotic--; and
    Line 53, "pRYP200" should read --pKYP200--.

UNITED STATES PATENT AND TRADEMARK OFFICE
CERTIFICATE OF CORRECTION

| | |
|---|---|
| PATENT NO. | : 7,422,878 B1 |
| APPLICATION NO. | : 10/110393 |
| DATED | : September 9, 2008 |
| INVENTOR(S) | : Koichiro Miyake et al. |

It is certified that error appears in the above-identified patent and that said Letters Patent is hereby corrected as shown below:

COLUMN 16

Line 14, "of" should be deleted; and
Line 37, "*amyloliquefacines*" should read --*amyloliquefaciens*--.

COLUMN 17

Line 34, "unexamined" should read --Unexamined--;
Line 37, "pCDMB" should read --pCDM8--; and
Line 61, "W. R." should read --W. H.--.

COLUMN 18

Line 54, "procaryote" should read --prokaryote--; and "eucaryote" should read --eukaryote--.

COLUMN 21

Line 1, "(1994);" should read --20 (1994);--;
Line 23, "(DEAE)-sepharose" should read --(DEAE)-Sepharose--; and
Line 51, "Example" should read --Examples--.

COLUMN 22

Line 53, "isoprenoid" should read --isoprenoids--.

COLUMN 27

Line 2, "*serevisiae*" should read --*cerevisiae*--.

COLUMN 29

Line 12, "unaerobic" should read --anaerobic--;
Line 15, "unaerobic" should read --anaerobic--; and
Line 16, "unaero-" should read --anaero- --.

UNITED STATES PATENT AND TRADEMARK OFFICE
CERTIFICATE OF CORRECTION

PATENT NO. : 7,422,878 B1
APPLICATION NO. : 10/110393
DATED : September 9, 2008
INVENTOR(S) : Koichiro Miyake et al.

It is certified that error appears in the above-identified patent and that said Letters Patent is hereby corrected as shown below:

<u>COLUMN 30</u>

Line 63, "rest" should read --test--.

Signed and Sealed this

Seventeenth Day of February, 2009

JOHN DOLL
*Acting Director of the United States Patent and Trademark Office*